United States Patent [19]
Goeddel et al.

[11] Patent Number: 5,747,023
[45] Date of Patent: May 5, 1998

[54] CANCER THERAPY USING LYMPHOTOXIN

[75] Inventors: David V. Goeddel, Hillsborough; Grace H. W. Wong, South San Francisco, both of Calif.

[73] Assignee: Genentech, Inc., South San Francisco, Calif.

[21] Appl. No.: 418,314

[22] Filed: Apr. 7, 1995

Related U.S. Application Data

[63] Continuation-in-part of Ser. No. 269,704, Jul. 1, 1994, abandoned.

[51] Int. Cl.$^6$ .......................... A61K 38/19; C07H 15/252; C07K 14/525
[52] U.S. Cl. ............................. 424/85.1; 514/12; 514/21; 530/351; 536/6.4
[58] Field of Search .......................... 424/85.1; 530/351; 514/12, 21; 536/6.4; 436/64

[56] References Cited

U.S. PATENT DOCUMENTS

| | | | |
|---|---|---|---|
| 4,405,601 | 9/1983 | McEntire et al. | 424/534 |
| 4,828,830 | 5/1989 | Wong | 424/85.5 |
| 4,861,587 | 8/1989 | Urbaschek et al. | 424/85.1 |
| 4,920,196 | 4/1990 | Aggarwal | 530/351 |
| 4,959,457 | 9/1990 | Bringman | 530/387.9 |
| 5,133,960 | 7/1992 | Schlick et al. | 424/85.1 |
| 5,277,903 | 1/1994 | Schlick et al. | 424/85.1 |

FOREIGN PATENT DOCUMENTS

| | | |
|---|---|---|
| 164965 | 12/1985 | European Pat. Off. . |
| 168214 | 1/1986 | European Pat. Off. . |
| 340005 | 11/1989 | European Pat. Off. . |
| 63-245692 | 10/1988 | Japan . |

OTHER PUBLICATIONS

Van Moorselaar et al. "Combined Effects of Tumor Necrosis Factor α & Radiation in the Treatment of Renal Cell Carcinoma Grown on Radon Spheroids" *Anticancer Res* 10 1769–1774 1990.

Regenass et al. "Antitumor Effects of TNF in Combination w/Chemotherapeutic Agents" *Int. J. Canc.* 39 266–273 1987.

Buckley et al., "Schedule–Dependent Enhanced Lethality with Combined Administration of Actinomycin D and Tumor Necrosis Factor in Mice" *J. Biological Response Modifiers* 8:287–296 (1989).

Mashiba et al.,"Augmentation of Antitumor Effect in Combined Use of Lymphotoxin and Antitumor Drug on MethA Tumors" *Immunobiology* 175(1–2):98 (1987).

Matsunaga et al., "Amplification of Cytotoxic Effect of Antitumor Drugs by Combined Use of Lymphotoxin" *Chemical Abstracts* (abstract only) 104(1):27 (1986).

Matsunaga et al., "Augmentation of in vitro cytotoxicity and in vivo tumor–inhibition by combined use of lymphotoxin-containing supernatants and antitumor drugs" *Cancer Letters* 20:21–28 (1983).

Mikami et al, "In vivo Effects of Recombinant Human Lymphotoxin on Human Medulloblastoma Xenograft: Enhancement of Antitumor Activity of Etoposide" *Biotherapy* 8:7–17 (1995).

*Autologous Bone Marrow Transplantation: Proceedings of the Third International Symposium,* Dicke et al., University of Texas M.D. Anderson Hospital (1987).

*Remington's Pharmaceutical Sciences,* Oslo et al., 16th edition, Mack Publishing Co. (1980).

Aggarwal, "Comparative Analysis of the Structure and Function of TNF–α and TNF–β" *Tumor Necrosis Factors: Structure, Function and Mechanism of Action,* Aggarwal and Vicek, eds., pp. 61–78 (1992).

Aggarwal et al., "Human Tumor Necrosis Factor" *Journal of Biological Chemistry* 260(4):2345–2354 (1985).

Aggarwal et al., "Lymphotoxin and Tumor Necrosis Factor: Qualitative and Quantitative Differences in Their Receptors and Signal Transduction in Various Cell Types" *Cytokines and Lipocortins in Inflammation and Differentiation,* Wiley–Liss, Inc. pp. 375–384 (1990).

Benjamin et al., "Human B–Cell TNF–β Microheterogeneity" *Lymphokine and Cytokine Research* 11(1):45–54 (1992).

Carswell et al., "An endotoxin–induced serum factor that causes necrosis of tumors" *Proc. Natl. Acad. Sci.* 72(9):3666–3670 (1975).

Cludts, "Cloning and Characterization of the Tandemly Arranged Bovine Lymphotoxin and Tumour Necrosis Factor–Alpha Genes" *Cytokine* 5(4):336–341 (Jul. 1993).

Dalmau et al., "Interleukin–1 and Tumor Necrosis Factor–Alpha as Radio–and Chemoprotectors of Bone Marrow" *Bone Marrow Transplantation* 12:551–563 (1993).

Fiers, "Precursor Structures and Structure–Function Analysis of TNF and Lymphotoxin" *Tumor Necrosis Factors,* Aggarwal and Vilcek, eds., pp. 79–92 (1992).

Fukushima et al., "N–Linked Sugar Chain Structure of Recombinant Human Lymphotoxin Produced by CHO Cells: The Functional Role of Carbohydrate as to Its Lectin–like Character and Clearance Velocity" *Archives of Biochemistry & Biophysics* 304(1):144–153 (1993).

Funahashi et al, "Tumour Growth Inhibition in Mice by Glycosylated Recombinant Human Lymphotoxin: Analysis of Tumor–Regional mononuclear Cells Involved with Its Action" *Br. J. Cancer* 67:447–455 (1993).

Funahashi et al., "Usefulness of Glycosylated Recombinant Human Lymphotoxin for Growth Inhibition of Human and Murine Solid Tumors and Experimental Metastasis in Mice" *Journal of Immunotherapy* 10:28–38 (1991).

(List continued on next page.)

*Primary Examiner*—Nancy Degen
*Attorney, Agent, or Firm*—Diane L. Marschang

[57] ABSTRACT

Methods and compositions are provided which include use of lymphotoxin (LT) and one or more other anti-cancer therapies for treating cancer in vivo or ex vivo. LT can be employed, for instance, with chemotherapy or radiation therapy to provide improved anti-cancer therapy.

24 Claims, 12 Drawing Sheets

OTHER PUBLICATIONS

Goeddel et al., "Tumor Necrosis Factors: Gene Structure and Biological Activities" *Cold Spring Harbor Symposia on Quantitative Biology* LI:597–609 (1986).

Goh, "Tumour Necrosis Factors in Clinical Practice" *Ann. Acad. Med. Singapore* 19:235–239 (1990).

Gray et al., "Cloning and expression of cDNA for human lymphotoxin, a lymphokine with tumour necrosis activity" *Nature* 312:721–724 (1984).

Hallahan et al. *Intl. J. Radiation Oncology, Biology, Physics* (Abstract No. 94) 27 (Suppl. 1, No. 184) (1993).

Hallahan et al., "The Effects of Cytokines on Tumor Cells" *Important Advances in Oncology* pp. 75–76 (1993).

Haranaka et al., "Antitumor Activity of Murine Tumor Necrosis Factor (TNF) Against Transplanted Murine Tumors and Heterotransplanted Human Tumors in Nude Mice" *Int. J. Cancer* 34:263–267 (1984).

Hussein et al., "Protection from Chemotherapy–Induced Alopecia in a Rat Model" *Science* 249:1564–1566 (1990).

Jeffes et al., "Human Alpha Lymphotoxin (LT): Studies Examining the Mechanism(s) of LT–Induced Inflammation and Tumor Destruction In Vivo" *Lymphokine Research* 6(2):141–149 (1987).

Kawatsu et al., "The Pharmacokinetic Pattern of Glycosylated Human Recombinant Lymphotoxin (LT) in Rats after Intravenous Administration" *J. Pharmacobio–Dyn.* 13:549–557 (1990).

Kawatsu et al., "Synergistic Antitumor Effect of Glycosylated Recombinant Human Lymphotoxin with Human Interferon–γ Lymphotoxin–Sensitive Human Tumor" *Journal of Interferon Research* 10:519–529 (1990).

Kircheis et al., "Differences in the Biological Activity of TNFα and TNFβ Correlate with Their Different Abilities for Binding to the Target Cells" *Eur. Cytokine Netw.* 3(4):381–390 (1992).

Kofler et al., "Size Heterogeneity of Human Lymphotoxin Is Due to O–Linked Glycosylation" *Lymphokine and Cytokine Research* 11(1):9–14 (1992).

Li et al., "Cloning and Expression of Murine Lymphotoxin cDNA" *J. of Immunology* 138(12):4496–4501 (Jun. 15, 1987).

Lipoldova et al., "Expression of the Gene for Tumor Necrosis Factor–β but Not for Tumor Necrosis Factor–α is Impaired in Tumor–Bearing Mice" *Cellular Immunology* 152:234–239 (1993).

Locksley et al., "Tumor Necrosis Factors α and β Differ in Their Capacities to Generate Interleukin 1 Release from Human Endothelial Cells" *J. of Immunology* 139(6):1891–1895 (Sep. 15, 1987).

Matsuyama et al., "Nucleotide Sequence of a cDNA Encoding Human Tumor Necrosis Factor β from B Lymphoblastoid Cell RPMI 1788" *FEBS Letters* 302(2):141–144 (May 1992).

Mikami et al., "Antitumor Effect of Recombinant Human Lymphotoxin on a Tumor Line of Human Malignant Glioma" *Hiroshima J. Med. Sci.* 38(3):103–107 (Sep. 1989).

Mordenti et al., "Interspecies Scaling of Clearance and Volume Distribution Data for Five Therapeutic Proteins" *Pharmaceutical Research* 8(11):1351–1359 (1991).

Nakata et al., "Combined Effect of PT–050 (Recombinant Human TNF) and Antitumor Drugs on Syngeneic Murine Tumors" *Jap. J. Cancer Chemo.* (English translation) 13:3186–3193 (1986).

Neta, "Radioprotection with Cytokines—Learning from Nature to Cope with Radiation Damage" *Cancer Cells* 3:391–396 (1991).

Neta et al., "Comparison of the In Vivo effects of rIL–1 and rTNF in radioprotection, induction of CSF and of acute phase reactants" *Fed. Proc.* (Abstract) 46(4):1200 (1987).

Neta et al., "Cytokines in therapy of radiation injury" *Blood* 72(3):1093–1095 (Sep. 1988).

Neta et al., "Interdependence of the radioprotective effects of human recombinant interleukin 1α, tumor necrosis factor α, granulocyte colony–stimulating factor, and murine recombinant granulocyte–macrophage colony–stimulating factor", *J. Immunol.*, 40(1):108–111 (1988).

Neta et al., "Interleukin 1 is a Radioprotector" *J. Immunol.* 136:2483–2485 (1986).

Nishiguchi et al., "Tumor Necrosis Factor as an Adjunct to Fractionated Radiotherapy in the Treatment of Murine Tumors" *Int. J. Radiation Oncology Biol. Phys.* 18:555–558 (1990).

Palladino, M. et al., "Characterization of the antitumor activities of human tumor necrosis factor–α and the comparison with other cytokines: induction of tumor–specific immunity" *J. Immunol.* 138:4023–4032 (1987).

Paul et al., "Lymphotoxin" *Ann. Rev. Immunol.*, 6:407–438 (1988).

Pennica et al., "Human tumour necrosis factor: precursor structure, expression and homology to lymphotoxin" *Nature* 312:724–729 (1984).

Pichyangkul et al., "Potentiation of Cytotoxic Effect of Lymphotoxin by Anti–Cancer Drugs and Elevated Temperatures" *Proceedings of the Society for Experimental Biology and Medicine* 183:231–236 (1986).

Ruddle, "Tumor Necrosis Factor (TNF–α) and Lymphotoxin (TNF–β)" *Current Opinion in Immunology* 4:327–332 (1992).

Ruddle et al., "Lymphotoxin, a Biologically Relevant Model Lymphokine" *Lymphokine Research* 2(1):23–31 (1983).

Ruddle et al., "Lymphotoxin: Cloning, Regulation and Mechanism of Killing" *Ciba Foundation Symposium* 131:64–82 (1987).

Seibel et al., "Phase I Study of Tumor Necrosis Factor–α and Actinomycin D in Pediatric Patients with Cancer: A Children's Cancer Group Study" *J. Immunotherapy* 16:125–131 (1994).

Sersa et al., "Anti–Tumor Effects of Tumor Necrosis Factor Alone or Combined with Radiotherapy" *Int. J. Cancer* 42:129–134 (1988).

Shakhov et al., "Structural Analysis of the Rabbit TNF Locus, Containing the Genes Encoding TNF–β (Lymphotoxin) and TNF–α (Tumor Necrosis Factor)" *Gene* 95:215–221.

Slordal et al., "Effect of Recombinant Murine Tumor Necrosis Factor on Hemopoietic Reconstitution in Sublethally Irradiated Mice" *J. Immunol.* 142:833–835 (1989).

Slordal et al., "Radioprotection by Murine and Human Tumor–Necrosis Factor: Dose–dependent Effects on Hematopoiesis in the Mouse" *European Journal of Haematology* 43:428–434 (1989).

Spriggs, "Tumor Necrosis Factor: Basic Principles and Preclinical Studies" *Biologic Therapy of Cancer*, DeVita et al., J.B. Lippincott Co. pp. 354–377 (1991).

Takeda et al, "Lymphotoxin and TNF Differ Greatly in Capacity to Induce Differentiation of Human Myeloblastic Leukemia ML–1 Cells" *Biochemistry and Molecular Biology International* 32(6):1109–1119 (Apr. 1994).

Trinchieri, "Effects of TNF and Lymphotoxin on the Hematopoietic System" *Immunology Series* 56:289–313 (1992).

Ulich et al., "Recombinant Human Alpha Lymphotoxin (Tumor Necrosis Factor–Beta) Induces Peripheral Neutrophilia and Lymphopenia in the Rat" *American Journal of Pathology* 128(1):5–12 (Jul. 1987).

Urbaschek et al., "Tumor necrosis factor induced stimulation of granulopoiesis and radioprotection" *Lymphokine Research* 6(3):179–186 (1987).

Voigt et al., "Natural Human Tumor Necrosis Factor Beta (Lymphotoxin)" *FEBS Letters* 314(1):85–88 (1992).

Wong et al., "Induction of manganous superoxide dismutase by tumor necrosis factor: possible protective mechanism" *Science* 242(4880):941–944 (1988).

Wong et al., "Tumor Necrosis Factor" *Human Monocytes*, Academic Press pp. 195–215 (1989).

Wong et al., "MnSOD Induction by TNF and Its Protective Role" *Tumor Necrosis Factors: The Molecules and their Emerging Role in Medicine*, Beutler, B., Raven Press pp. 473–484 (1992).

Wong et al., "Protective Roles of MnSOD, TNF–$\alpha$, TNF–$\beta$ and D–Factor (LIF) in Radiation Injury" *Eicosanoids and Other Bioactive Lipids in Cancer, Inflammation and Radiation Injury*, (Ch. 70), S. Nigam pp. 353–357 (1993).

Yamanaka et al., "Identity of Human B–cell Line Cytotoxic Lymphokine With Tumor Necrosis Factor Type $\beta$" *Immunology* 86:1343–1347 (1989).

Yuhas et al., "Differential chemoprotection of normal and malignant tissues" *J. Natl. Cancer Institute* 42(2):331–335 (Feb. 1969).

Control

LT

Clonogenic Assay ($10^5$ cells)

CANCER THERAPY USING LYMPHOTOXIN

RELATED APPLICATIONS

This application is a continuation-in-part application of U.S. application Ser. No. 08/269,704 filed Jul. 1, 1994, now abandoned, incorporated herein by reference.

FIELD OF THE INVENTION

The invention relates generally to the use of lymphotoxin and one or more other anti-cancer therapies, such as chemotherapy and radiation therapy, to treat cancer.

BACKGROUND OF THE INVENTION

Tumor necrosis factor ("TNF") was first identified as a serum-derived factor which was cytotoxic for several transformed cell lines in vitro and caused necrosis of certain tumors in vivo. A similar factor was identified and referred to as lymphotoxin ("LT"). Due to observed similarities between TNF and LT in the early 1980's, it was proposed that TNF and LT be referred to as TNF-α and TNF-β, respectively. Scientific literature thus makes reference to both nomenclatures. As used in the present application, the term "TNF" refers to tumor necrosis factor or TNF-α, and the term "LT" refers to lymphotoxin or TNF-β.

Cloning of the TNF and LT proteins and further characterization of their respective biological activities revealed that the proteins differ in many aspects. [Aggarwal et al., *Cytokines and Lipocortins in Inflammation and Differentiation*, Wiley-Liss, Inc. 1990, pp. 375–384]. For instance, LT is a secreted, soluble protein of approximately 20 kDa (25 kDa if N- and O-glycosylated). TNF, in contrast, has no site for glycosylation and is synthesized with an apparent transmembrane domain that results in the original protein transcript being cell associated. Proteolysis of the cell associated TNF protein results in the release of the soluble form of the protein having a molecular weight of approximately 19 kDa. TNF is produced primarily by activated macrophages whereas LT is produced by activated lymphocytes. [Wong et al., *Tumor Necrosis Factors: The Molecules and their Emerging Role in Medicine*, Beutler, B., ed., Raven Press (1991), pp. 473–484]. The sequences encoding TNF and LT also differ. TNF and LT share only approximately 32% amino acid sequence identity. Regarding the different biological activities of TNF and LT, TNF increases production of endothelial cell interleukin-1 ("IL-1") whereas LT has little effect. Further, TNF induces production of macrophage colony stimulating factor from macrophages whereas LT has no effect. These and other biological activities are discussed in Aggarwal, *Tumor Necrosis Factors: Structure, Function and Mechanism of Action*, Aggarwal and Vicek, eds. (1992), pp. 61–78.

TNF and LT are described further in the review articles by Spriggs, "Tumor Necrosis Factor: Basic Principles and Preclinical Studies," *Biologic Therapy of Cancer*, DeVita et al., eds., J. B. Lippincott Company (1991) Ch. 16, pp. 354–377; Ruddle, *Current Opinion in Immunology*, 4:327–332 (1992); Wong et al., "Tumor Necrosis Factor," *Human Monocytes*, Academic Press (1989), pp. 195–215; and Paul et al., *Ann. Rev. Immunol.*, 6:407–438 (1988).

Although increased numbers of cancer treatments have become available in recent years, a need exists for improved types of cancer therapy and therapy protocols. Some chemotherapies and radiation therapies show relatively promising results but are often limited in terms of dosages which can be tolerated by patients. Further, cancer treatments are often accompanied by adverse side effects, such as destruction of normal or healthy tissues and cells, impairment of the lymphoid and hematopoietic systems, or hair loss (also referred to as alopecia).

As discussed above, TNF has been reported to have certain anti-cancer activity. [see, e.g., Haranaka et al., *Int. J. Cancer*, 34:263–267 (1984); Nishiguchi et al., *Int. J. Radiation Oncology*, 18:555–558 (1990)]. In particular, the effects of TNF in certain cancer treatments have been reported. TNF, for example, has been described as having certain protective effects against radiation under particular experimental conditions. U.S. Pat. No. 4,861,587, issued Aug. 29, 1989 to Urbaschek et al. discloses the use of TNF in the treatment of radiation damage. The effect of TNF in protecting bone marrow precursor cells from irradiation has also been described. [See, e.g., Dalmau et al., *Bone Marrow Transplantation*, 12:551–563 (1993); Wong et al., *Science*, 242:941–944 (1988); Neta et al., *J. Immunol.*, 140:108 (1988); Neta et al., *Blood*, 72:1093 (1988); Trinchieri, "Effects of TNF and Lymphotoxin on the Hematopoietic System," *Immunology Series*, 56:289–313 (1992); Neta et al., *Cancer Cells*, 3:391–396 (1991)]. Other references discussing such effects of TNF are described more particularly below.

Neta et al., *J. Immunol.*, 136:2483 (1987) teach that administration of recombinant human TNF protected lethally irradiated normal mice from death.

Slordal et al. teach that single intravenous administration of murine TNF to BALB/c mice 20 hours before sublethal total body irradiation protected against radiation induced neutropenia and accelerated regeneration of hematopoietic precursors and normalization of peripheral blood cell counts. [Slordal et al., *J. Immunol.*, 142:833 (1989); Slordal et al., *Eur. J. Haematol.*, 43:428–434 (1989)].

Urbaschek et al. report that TNF reduced the lethality rate of an LD 75/30 (dose of radiation that kills 75% of mice in 30 days) to an LD 40/30 when injected in C3H/HeJ mice either 24 hours before or after exposure to whole-body radiation. [Urbaschek et al., *Lymphokine Res.*, 6:179 (1987)].

Sersa et al. also report on the effect of administering recombinant human TNF with ionizing radiation. [Sersa et al., *Int. J. Cancer*, 42:129–134 (1988)]. Specifically, Sersa et al. examined the effects of the TNF on murine tumors in mice when multiple intravenous TNF injections were administered after local tumor irradiation. Sersa et al. report that the TNF and local tumor irradiation caused a delay in tumor growth. [Id.]. Reduced radiation damage to bone marrow progenitor cells was also observed. [Id.].

Neta et al., *Fed. Proc.*, 46:1200 (abstract) (1987) describe the radioprotective effects of IL-1 and TNF. Neta et al. teach that following intraperitoneal administration, 75-fold higher doses of TNF than of IL-1 were required to obtain significant radioprotection, and that even at optimal doses, TNF was less effective than IL-1 in protecting against increasing doses of radiation. [Id.].

Some investigators have reported that under certain conditions, TNF may sensitize particular tumor cells to radiation. Hallahan et al. teach that addition of TNF to SCC-61 tumor cells in vitro 4–8 hours prior to irradiation enhanced tumor cell killing. [Hallahan et al., "The Effects of Cytokines on Tumor Cells," *Important Advances in Oncology*, pp. 75–76 (1993); in *Intl. J. Radiation Oncology, Biology, Physics*, 27:Suppl. 1, No. 184, Abstract No. 94 (1993), Hallahan et al. also describe administering TNF to patients 4 hours prior to irradiation on consecutive days for at least two weeks]. TNF pretreatment may also render the human leukemic cell lines HL-60, K562, and U937 more sensitive to radiation. [Wong et al., in *Eicosanoids and Other Bioactive Lipids in Cancer, Inflammation and Radiation Injury*, S. Nigam, ed., (1993) Ch. 70 pp. 353–357].

Other investigators, however, observed no such sensitizing effect by TNF. Sersa et al. report that TNF did not affect tumor cell radiosensitivity. [Sersa et al., supra].

The effects of TNF in combination with certain chemotherapy drugs have been the subject of further reports. Seibel et al., *J. Immunotherapy*, 16:125–131 (1994) describe administration of TNF in combination with Actinomycin D to pediatric cancer patients. Some investigators have hypothesized that it may be possible to enhance the therapeutic effects of the chemotherapy agent by simultaneous clinical use of recombinant TNF, and decrease the effective dosage of the chemotherapy agent so that side effects be reduced. [Nakata et al., *Jap. J. Cancer Chemo.*, 13:3186–3193 (1986)].

To date, the use and effects of LT in cancer treatments have not been fully examined. In particular, there is little known about the therapeutic effects of LT and radiation therapy or chemotherapy. Pretreatment of normal C3H/HeJ mice by intraperitoneal injection of LT was reported to increase survival rate following lethal doses of radiation. [Wong et al., *Eicosanoids and Other Bioactive Lipids in Cancer, Inflammation and Radiation Injury*, supra].

SUMMARY OF THE INVENTION

The invention provides methods of treating a mammal having cancer. In the methods, an effective amount of LT and one or more other anti-cancer therapies are administered to a mammal diagnosed as having cancer. The one or more other anti-cancer therapies may include chemotherapy or radiation therapy.

The invention also provides methods of reducing chemotherapy or radiation therapy induced bone marrow damage in mammals. In the methods, an effective amount of LT and chemotherapy or radiation therapy are administered to a mammal diagnosed as having cancer.

The invention also provides methods of reducing chemotherapy or radiation therapy induced alopecia in mammals. In the methods, an effective amount of LT and chemotherapy or radiation therapy are administered to a mammal diagnosed as having cancer.

The invention also provides methods of treating cancer comprising exposing cancer cells or tissues containing cancer cells to LT and chemotherapy or radiation therapy ex vivo. The cancer cells or tissues containing cancer cells may include bone marrow, and the bone marrow is exposed to the LT and chemotherapy or radiation therapy prior to being transplanted in a mammal.

The invention further provides articles of manufacture and kits that can be employed in treating cancer. The articles of manufacture and kits include a container, a label on the container, and a composition contained within the container. The label on the container indicates that the composition can be used with chemotherapy or radiation therapy to treat cancer, and the active agent in the composition comprises LT.

Applicants have surprisingly found that use of LT in combination with chemotherapy or radiation therapy provides improved anti-cancer therapy. More particularly, it was found that when LT and chemotherapy or radiation therapy is employed to treat cancer, LT protects normal or healthy cells (i.e., non-cancerous cells) from the chemotherapy or radiation treatment. Protection of the normal or healthy cells is manifested, for instance, by increased numbers of viable cells and less toxicity following the chemotherapy or radiation therapy. Further, it was found that the LT sensitizes cancer cells to the chemotherapy or radiation. It is believed that the LT renders the cancer cells more susceptible to the chemotherapy or radiation therapy. Thus, for instance, cancer cells which are resistant to particular forms of chemotherapy may be rendered susceptible to the chemotherapy by exposing the cells to lymphotoxin. Administration of LT along with chemotherapy and/or radiation therapy can prevent or reduce adverse side effects which often accompany, or are induced by, chemotherapy and radiation therapy. In accordance with the invention, increased, and more effective, doses of chemotherapy and/or radiation therapy may be administered and tolerated, thereby improving the overall anti-cancer therapy.

DETAILED DESCRIPTION OF THE PREFERRED EMBODIMENTS

1. Definitions

Figure 1:
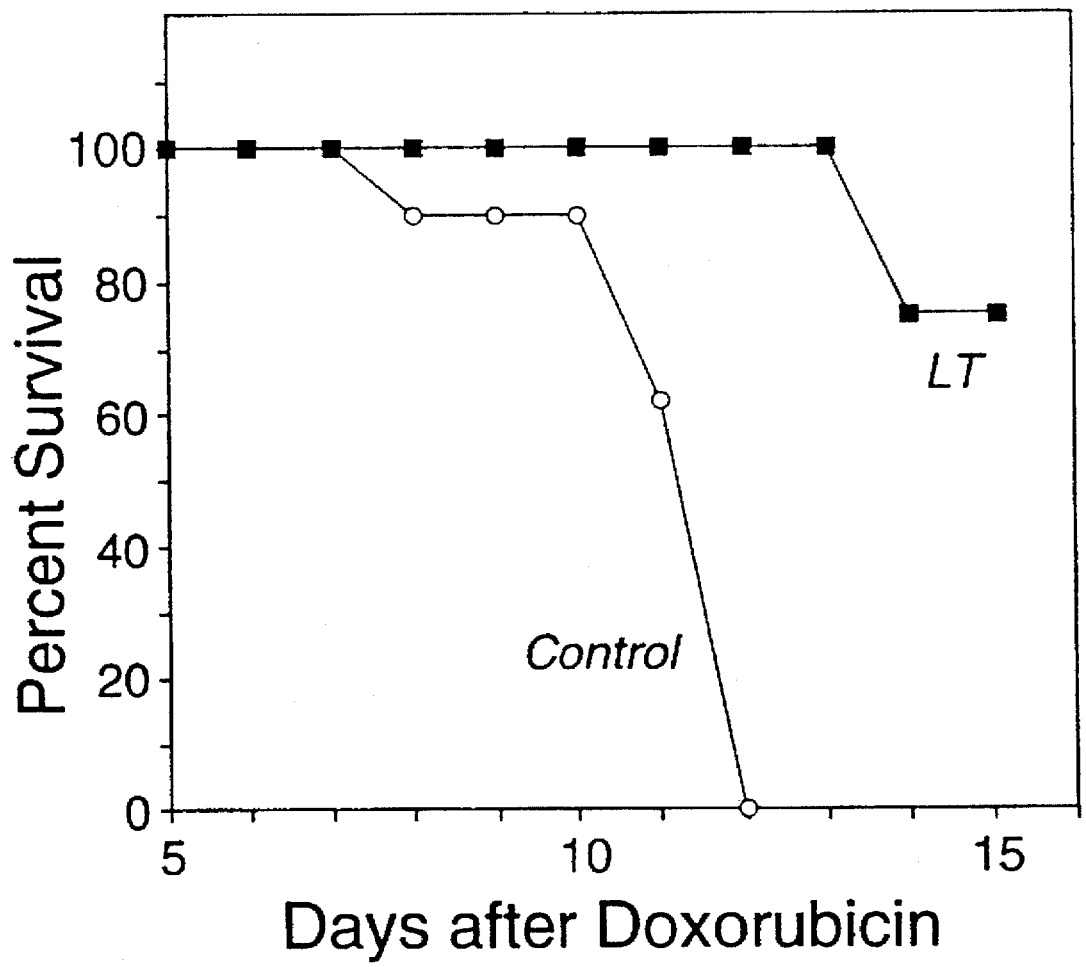
FIG. 1 is a graph showing the effect of LT and Doxorubicin on survival of normal rats.

As used herein, the term "lymphotoxin" ("LT") refers to a polypeptide having a region demonstrating substantial structural amino acid homology with at least a portion of the sequence comprising amino acids 1–171 of human lymphotoxin. The DNA sequence encoding human lymphotoxin and its corresponding amino acid sequence are published in EP 164,965 A2 and Gray et al., Nature, 312:721–724 (1984). Substantial structural amino acid homology generally means that greater than about 60 percent, and usually greater than about 70 percent of the amino acid residues in the polypeptide are the same or conservative substitutions for the corresponding residues in the sequence for human lymphotoxin. The term lymphotoxin includes the mature, pre, pre-pro, and pro forms of the molecule, either purified from a natural source, chemically synthesized or recombinantly produced. The lymphotoxin of the invention includes leucyl amino-terminal lymphotoxin and histidyl amino-terminal lymphotoxin (such as described in EP 164,965 A2), lymphotoxin aggregates (such as trimers), and lymphotoxin variants including (a) fusion proteins wherein a heterologous polypeptide or protein is linked to the amino and/or carboxyl-terminal amino acids of lymphotoxin, (b) lymphotoxin fragments, especially fragments of pre lymphotoxin in which any amino acid between −34 and +23 is the amino-terminal amino acid of the fragment, (c) lymphotoxin mutants wherein one or more amino acid residues are substituted, inserted or deleted, and (d) methionyl or modified methionyl (such as formyl methionyl or other blocked methionyl species) amino-terminal derivatives. The term lymphotoxin specifically includes the lymphotoxin species disclosed in EP 164,965 A2, published Dec. 18, 1985.

Lymphotoxin as defined herein specifically excludes human tumor necrosis factor (TNF-α) or its animal analogues [such as described by Pennica et al., Nature, 312:724–729 (1984) and Aggarwal et al., J. Biol. Chem., 260:2345–2354 (1985)].

The terms "amino acid" and "amino acids" refer to all naturally occurring L-α-amino acids. This definition is meant to include norleucine, ornithine, and homocysteine. The amino acids are identified by either the single-letter or three-letter designations:

| Asp | D | aspartic acid | Ile | I | isoleucine |
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

Substitution of an amino acid with an amino acid(s) having a side chain that is similar in charge and/or structure to that of the native molecule is referred to as a conservative substitution, and would not be expected to substantially alter either the structure of the backbone of the molecule or the charge or hydrophobicity of the molecule in the area of the substitution.

The terms "treating," "treatment," and "therapy" refer to curative therapy, prophylactic therapy, and preventative therapy.

The terms "cancer" and "cancerous" refer to or describe the physiological condition in mammals that is typically characterized by unregulated cell growth. Examples of cancer include but are not limited to, carcinoma, lymphoma, blastoma, sarcoma, and leukemia. More particular examples of such cancers include squamous cell carcinoma, small-cell lung cancer, non-small cell lung cancer, pancreatic cancer, glioblastoma multiforme, cervical cancer, bladder cancer, hepatoma, breast cancer, colon carcinoma, and head and neck cancer.

The term "mammal" refers to any mammal classified as a mammal, including humans, cows, horses, dogs, cats, rats and mice. In a preferred embodiment of the invention, the mammal is a human.

2. Methods and Compositions of the Invention

The present invention provides methods and compositions for treating cancer which include lymphotoxin, referred to hereinafter as "LT". The LT useful in the practice of the present invention can be prepared in a number of ways. For instance, the LT can be prepared using an isolated or purified form of LT from natural sources or from cell lines. Methods of isolating or purifying LT are known in the art and are described, for example, in U.S. Pat. No. 4,920,196. Using the methods described in U.S. Pat. No. 4,920,196, human LT can be purified to a specific activity of at least about $10^6$ units/mg protein. Alternatively, LT can be chemically synthesized or produced using recombinant techniques known in the art and described further in U.S. Pat. No. 4,959,457 and EP 164,965 A2. The present invention is not limited to use of human LT. Other mammalian species of LT, such as murine or rabbit, may be employed. In a preferred embodiment, human LT is employed for treating humans having cancer.

In accordance with a first embodiment of the invention, methods are provided in which LT and one or more other anti-cancer therapies are administered to a mammal diagnosed as having cancer. In a preferred embodiment, LT is administered to the mammal along with chemotherapy, radiation therapy, or both chemotherapy and radiation therapy. It is of course contemplated that the methods and compositions of the invention can be employed in combination with still other therapeutic techniques such as surgery.

The LT is preferably administered to the mammal in a pharmaceutically-acceptable carrier. Suitable carriers and their formulations are described in Remington's Pharmaceutical Sciences, 16th ed., 1980, Mack Publishing Co., edited by Oslo et al. Typically, an appropriate amount of a pharmaceutically-acceptable salt is used in the formulation to render the formulation isotonic. Examples of the pharmaceutically-acceptable carrier include saline, Ringer's solution and dextrose solution. The pH of the solution is preferably from about 5 to about 8, and more preferably from about 7.4 to about 7.8. It will be apparent to those persons skilled in the art that certain carriers may be more preferable depending upon, for instance, the route of administration and concentration of LT being administered.

The LT can be administered to the mammal by injection (e.g., intravenous, intraperitoneal, subcutaneous, intramuscular), or by other methods such as infusion that ensure its delivery to the bloodstream in an effective form. Local or intravenous injection is preferred.

Effective dosages and schedules for administering LT may be determined empirically, and making such determinations is within the skill in the art. It is presently believed that an effective dosage or amount of human LT in mice and rats is in the range of about 50 µg/kg/day to about 500 µg/kg/day.

Interspecies scaling of dosages can be performed in a manner known in the art, e.g., as disclosed in Mordenti et al., *Pharmaceut. Res.*, 8:1351 (1991). Those skilled in the art will understand that the dosage of LT that must be administered will vary depending on, for example, the mammal which will receive the LT, the route of administration, and other drugs being administered to the mammal. The skilled clinician will understand, for instance, that lower dosages of human LT will likely be effective in humans as compared to human LT in mice and rats. Further, the skilled clinician will understand that intravenous administration of LT will likely require lower dosages as compared to intraperitoneal administration.

The one or more other anti-cancer therapies administered to the mammal include but are not limited to, chemotherapy and radiation therapy. Anti-cancer therapies such as immunoadjuvants and cytokines may also be employed, including interleukins (e.g., IL-1, IL-2, IL-3, IL-6), leukemia inhibitory factor, interferons, TGF-beta, erythropoietin and thrombopoietin. As used in the present application, the term "one or more other anti-cancer therapies" specifically excludes LT and TNF.

Chemotherapy contemplated by the invention includes chemical substances or drugs which are known in the art and are commercially available, such as Doxorubicin, 5-Fluorouracil, Cytosine arabinoside ("Ara-C"), Cyclophosphamide, Thiotepa, Busulfan, Cytoxin, Taxol, Methotrexate, Cisplatin, Melphalan, Vinblastine and Carboplatin. Preparation and dosing schedules for such chemotherapy may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992).

The chemotherapy is preferably administered in a pharmaceutically-acceptable carrier, such as those described above for LT. The mode of administration of the chemotherapy may be the same as employed for the LT or it may be administered to the mammal via a different mode. For example, the LT may be injected while the chemotherapy is administered orally to the mammal. Administration of LT and chemotherapy to a mammal is described in further detail in Example 1 below.

Radiation therapy can be administered to the mammal according to protocols commonly employed in the art and known to the skilled artisan. Such therapy may include cesium, iridium, iodine, or cobalt radiation. The radiation therapy may be whole body irradiation, or may be directed locally to a specific site or tissue in or on the body, such as the lung, bladder, or prostate. Typically, radiation therapy is administered in pulses over a period of time from about 1 to about 2 weeks. The radiation therapy may, however, be administered over longer periods of time. For instance, radiation therapy may be administered to mammals having head and neck cancer for about 6 to about 7 weeks. Optionally, the radiation therapy may be administered as a single dose or as multiple, sequential doses.

The LT and one or more other anti-cancer therapies may be administered to the mammal concurrently or sequentially. Preferably, administration is sequential, and more preferably, LT is administered to the mammal prior to the administration of the other anti-cancer therapy. In an even more preferred embodiment, at least two doses of LT are administered to the mammal prior to administration of chemotherapy and/or radiation therapy. Such LT pretreatment is described in further detail in the Examples below.

The skilled medical practitioner can determine empirically the appropriate doses of chemotherapy and/or radiation therapy useful herein. It is believed that increased doses of chemotherapy and/or radiation therapy may be administered and tolerated by the mammal when LT is administered prior to the chemotherapy and/or radiation therapy. (See, e.g., FIGS. 6 and 8).

Following administration of LT and one or more other anti-cancer therapies to the mammal, the mammal's cancer and physiological condition can be monitored in various ways well known to the skilled practitioner. For instance, tumor mass may be observed physically or by standard x-ray imaging techniques.

It is appreciated by those in the art that anti-cancer therapies such as chemotherapy and radiation therapy typically induce or are accompanied by adverse side effects in the mammal being treated. Examples of such adverse side effects include hair loss (also known as alopecia) and organ toxicity. Bone marrow damage, in addition, is often a result of such anti-cancer therapy, leading to blood diseases like thrombocytopenia. Applicants have found that the methods and compositions of the invention can prevent or reduce such side effects by selectively killing cancer cells without destroying normal or healthy cells.

In accordance with another embodiment of the invention, LT and one or more other anti-cancer therapies are employed to treat cancer cells ex vivo. It is contemplated that such ex vivo treatment may be useful in bone marrow transplantation and particularly, autologous bone marrow transplantation. For instance, treatment of cells or tissue(s) containing cancer cells with LT and one or more other anti-cancer therapies, such as described above, can be employed to deplete or substantially deplete the cancer cells prior to transplantation in a recipient mammal.

Cells or tissue(s) containing cancer cells are first obtained from a donor mammal. The cells or tissue(s) may be obtained surgically and preferably, are obtained aseptically. In the method of treating bone marrow for transplantation, bone marrow is obtained from the mammal by needle aspiration. The cells or tissue(s) containing cancer cells are then treated with LT and one or more other anti-cancer therapies, such as described above. Preferably, the cells or tissue(s) containing cancer cells are treated with LT and chemotherapy and/or radiation therapy, as described above. Bone marrow is preferably fractionated to obtain a mononuclear cell fraction (such as by centrifugation over ficoll-hypaque gradient) prior to treatment with LT and chemotherapy and/or radiation therapy.

The treated cells or tissue(s) can then be infused or transplanted into a recipient mammal. The recipient mammal may be the same individual as the donor mammal or may be another, heterologous mammal. For an autologous bone marrow transplant, the mammal is treated prior to the transplant with an effective dose of radiation or chemotherapy as known in the art and described for example in *Autologous Bone Marrow Transplantation: Proceedings of the Third International Symposium*, Dicke et al., eds., University of Texas M.D. Anderson Hospital and Tumor Institute (1987).

In accordance with another embodiment of the invention, there is provided an article of manufacture and kit containing materials useful for treating cancer. The article of manufacture comprises a container with a label. Suitable containers include, for example, bottles, vials, and test tubes. The containers may be formed from a variety of materials such as glass or plastic. The container holds a composition which is effective for treating cancer. The active agent in the composition is LT, and preferably is recombinant human LT. The label on the container indicates that the composition is used in combination with chemotherapy and/or radiation therapy for treating cancer, and may also indicate directions for in vivo or ex vivo use, such as those described above.

The kit of the invention comprises the container described above and a second container comprising a suitable diluent or buffer. It may further include other materials desirable from a commercial and user standpoint, including other buffers, filters, needles, syringes, and package inserts with instructions for use.

The invention will be more fully understood by reference to the following examples. They should not, however, be construed as limiting the scope of the invention. All reference citations herein are incorporated by reference.

EXAMPLES

The following Examples describe various in vitro and in vivo studies using LT. The LT used in these Examples was human histidyl amino-terminal lymphotoxin (approximately 16 kDa and having amino acids 24–171 of human lymphotoxin) produced in accordance with the recombinant methods described in EP 164,965 A2. The expressed LT was precipitated using polyetheneimine (PEI) precipitation and ammonium sulfate precipitation and then purified by column chromatography. The LT was chromatographed sequentially on silica gel, hydroxylapatite, and Sephacryl S-200. The LT was then sterile filtered (using a 22 µm filter), diluted in 0.1M Tris-HCl buffer (pH 7.8) at a concentration of 0.6 mg/ml, and stored at 4° C.

The TNF used in the Examples was human TNF produced in accordance with the recombinant methods described in EP 168,214 published Jan. 1, 1986 and Pennica et al., *Nature*, 312:724–729 (1984). The expressed TNF was precipitated using PEI precipitation and purified by column chromatography. The TNF was chromatographed sequentially on silica gel, DEAE fast flow sepharose, carboxymethyl cellulose (CM-52), Mono S cation exchange resin, and Sephacryl S-200. The TNF was then sterile filtered (using a 22 µm filter), diluted in phosphate buffered saline (pH 7.0) at a concentration of 0.5 mg/ml, and stored at 4° C.

The cell lines referred to in the Examples by "ATCC" numbers were obtained from the American Type Culture Collection, Rockville, Md.

Example 1: Effects of LT and Chemotherapy in Vivo

A. Effect on Survival

Seven day old rats (obtained from Harlan Sprague Dawley) were treated with LT and Doxorubicin. Doxorubicin (also referred to as Adriamycin®) (purchased from Adria Pharmaceuticals) was injected intraperitoneally (0.1 ml/rat) for seven consecutive days (Day 0 to Day 6) at a dose of 2 mg/kg/day. Rats were injected intraperitoneally with LT at a dose of 1 µg/0.1 ml/rat/day. The LT was administered at −2 Days and −1 Day prior to commencing Doxorubicin treatment on Day 0. Administration of LT continued from Day 0 through Day 6. Control animals were treated similarly except that 0.1 ml sterile phosphate buffered saline ("PBS") was injected intraperitoneally instead of LT. Survival was monitored daily until Day 15.

The results are shown in FIG. 1. The LT-Doxorubicin treated group showed 100% survival at Day 12 and 80% survival on Day 15. The control group had 0% survival at Day 12.

B. Effect on Bone Marrow

Figure 2A:
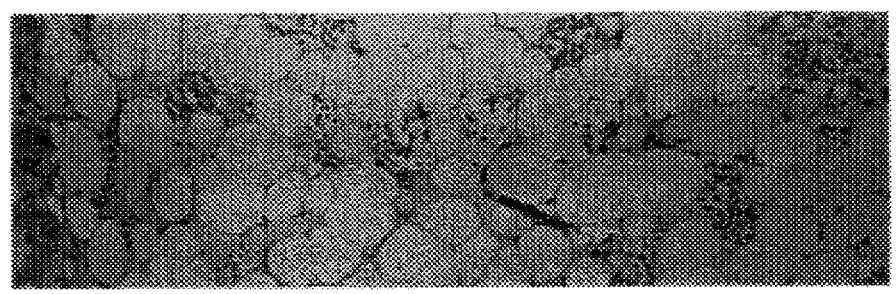
FIGS. 2A–2B are photographs comparing LT and Doxorubicin treated rat bone marrow (FIG. 2B) to control rat bone marrow (treated only with Doxorubicin) (FIG. 2A).
Figure 2B:
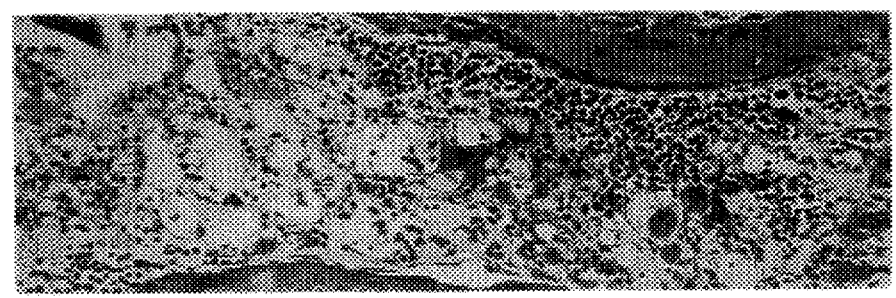

One of the LT-Doxorubicin treated rats and one of the control rats described in Example 1, Section A above were sacrificed on Day 9. Bone sternums from the rats were dissected, and marrow cells from the sternums were fixed with 10% neutral-buffered Formalin and embedded in paraffin wax. Approximately 4 µm sections of the embedded cells were stained with hematoxylin and eosin on microscope slides. Histological analysis showed that the rat receiving LT and Doxorubicin had granulocyte progenitor cells and megakaryocytes that were protected from the chemotherapy induced toxicity whereas very few cells were found in sternum marrow obtained from the control rat. (See FIG. 2).

C. Effect on Alopecia

Eight day old rats (obtained from Harlan Sprague Dawley) were treated with LT and cytosine-arabinoside ("Ara-C") in accordance with the protocol outlined in Example 1, Section A above except that Ara-C (purchased from Upjohn) was injected intraperitoneally (0.1 ml/rat) at a dose of 20 mg/kg/day from Day 0 to Day 6. Control animals were similarly treated except that 0.1 ml sterile PBS was injected instead of LT.

On Day 15, the degree of alopecia observed for the control and LT-Ara-C treated animals was rated on a scale of 0 to 4+, with 0 representing no observable hair loss and 4+ representing substantial balding of the animal. The results are shown in Table 1 below. Enhanced protection from alopecia occurred in the LT-Ara-C treated group with 9/10 animals demonstrating no observable hair loss.

TABLE 1

| TREATMENT | DEGREE OF ALOPECIA | | | | |
|---|---|---|---|---|---|
| | 0 | 1+ | 2+ | 3+ | 4+ |
| Control (Ara-C only) | | 1 | 1 | 5 | 3 |
| LT and Ara-C | 9 | 1 | | | |

Example 2: Effects of LT and Chemotherapy in Vitro

A. Effect on U-937 Tumor Cells

U-937 cells (human histiocystic lymphoma cell line, ATCC No. CRL 1593) were cultured in RPMI-1640 medium in 96 well tissue culture plates at a concentration of $10^5$ cells/well. The cell cultures were treated with (1) Doxorubicin (50 µg/ml); (2) LT (0.1 µg/ml); (3) TNF (0.1 µg/ml); (4) LT and Doxorubicin; or (5) TNF and Doxorubicin. Control cultures contained RPMI-1640 medium.

Figure 3:
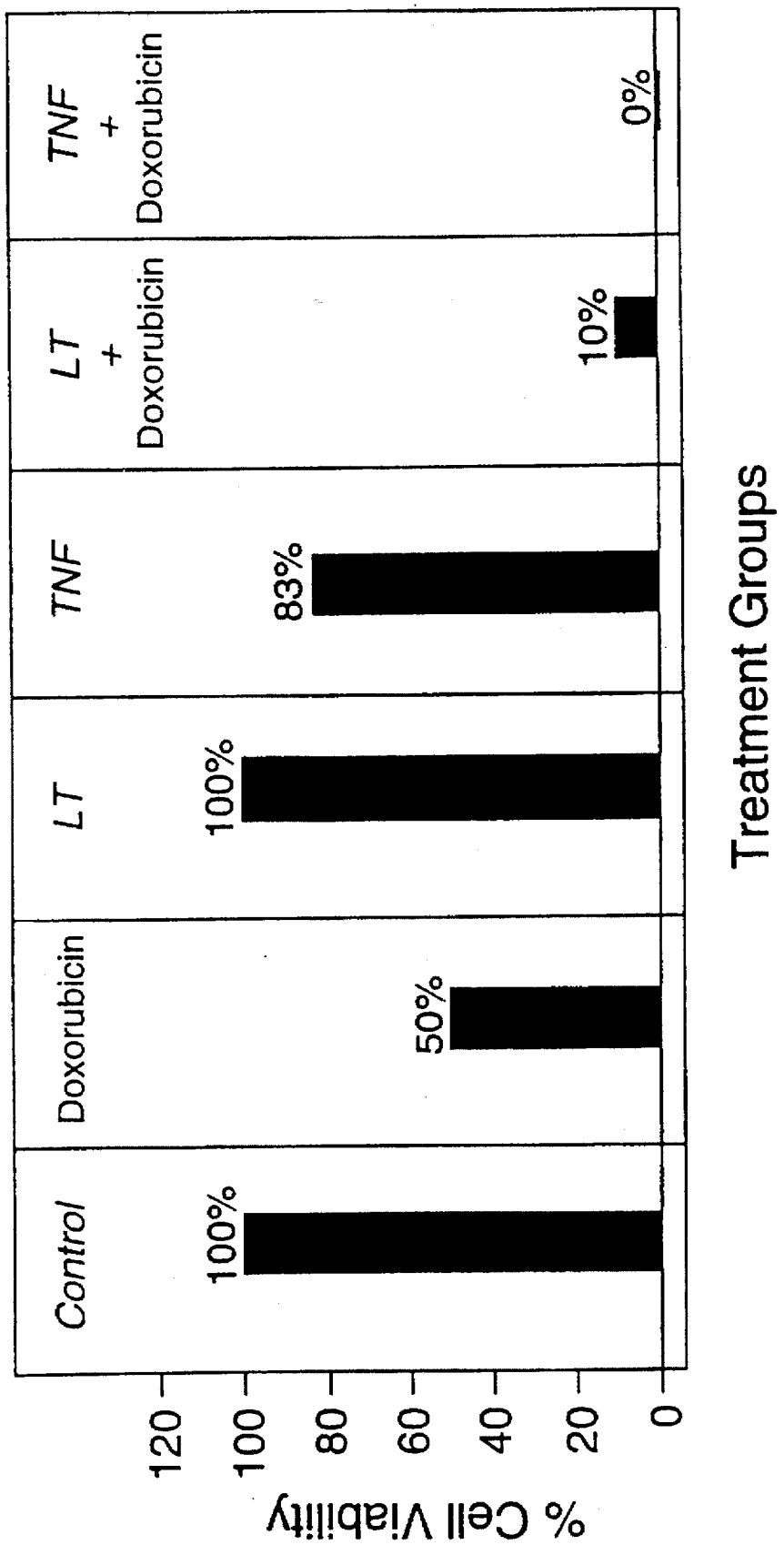
FIG. 3 is a bar diagram comparing the effects of Doxorubicin, LT, TNF, LT and Doxorubicin, and TNF and Doxorubicin on viability of U-937 human histiocystic lymphoma cells in vitro.

The tissue culture plates containing the test cultures and control cultures were then incubated at 37° C. for 24 hours. After the incubation, the cells were tested for viability using trypan blue dye (diluted to 0.4% in PBS) exclusion. The results are shown in FIG. 3. Both LT and TNF enhanced sensitivity of the U-937 cells to the Doxorubicin.

B. Effect on ME-180 Tumor Cells

ME 180 cells (human epidermoid carcinoma cell line, ATCC No. HTB 33) were cultured in RPMI-1640 medium in 96 well tissue culture plates at a concentration of $10^5$ cells/ml. The cell cultures were treated with either 0.1 µg/ml LT and varying dilutions of Doxorubicin (200 µg/ml, 100 µg/ml, 50 µg/ml, and 25 µg/ml and 2-fold dilutions thereof) or the varying dilutions of Doxorubicin alone. RPMI-1640 medium or LT (0.1 µg/ml) was added to the control cultures.

The tissue culture plates containing the test cultures and control cultures were then incubated at 37° C. for 30 hours. Following incubation, the cells were stained with crystal violet (0.5% crystal violet in 20% methanol).

Figure 4:
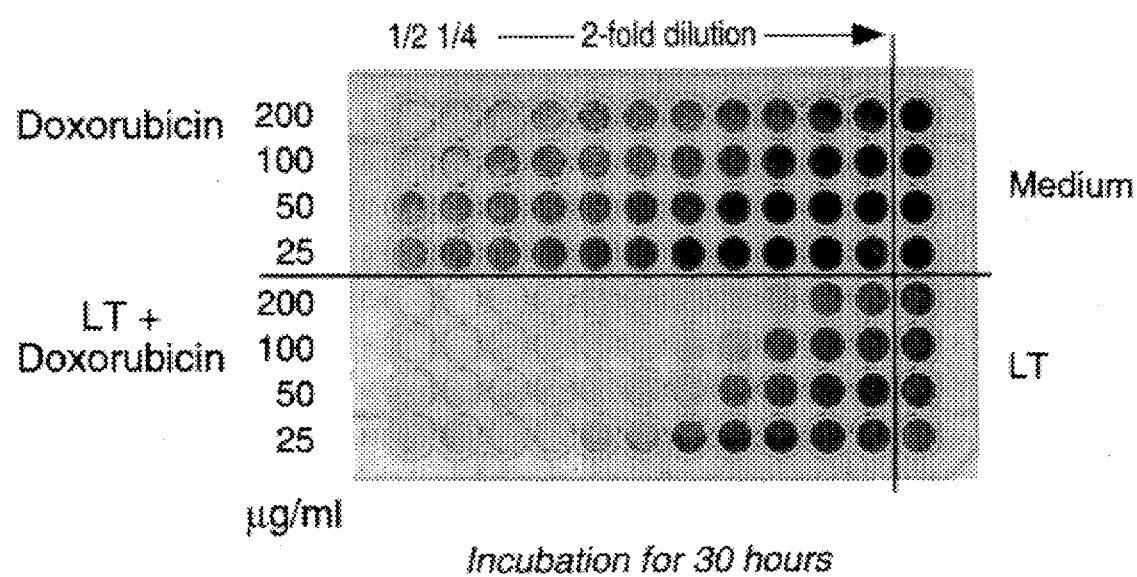
FIG. 4 is a photograph of crystal violet-stained ME 180 cervical carcinoma cells cultured in vitro with Doxorubicin, LT, medium only (control) or LT and Doxorubicin.

The stained cultures showed that co-cultivation of the ME 180 cells with LT and Doxorubicin enhanced cell killing significantly. (FIG. 4). Viable cells were detected in the cell cultures treated with Doxorubicin alone at concentrations of Doxorubicin as high as 50–100 µg/ml. In contrast, no viable cells were identified in the cultures treated with LT and Doxorubicin at concentrations of Doxorubicin as low as 3–6 µg/ml. (FIG. 4).

Similarly conducted experiments using BxPC-3 cells (human pancreatic adenocarcinoma cell line, ATCC No. CRL 1687), Su.86.86 cells (human pancreatic carcinoma cell line, ATCC No. CRL 1837), A549 cells (human lung carcinoma cell line, ATCC No. CCL 185), and L929 cells (murine lung fibroblast cell line, ATCC No. CCL 1) also showed that LT and Doxorubicin treatment resulted in enhanced killing of the tumor cells and that Doxorubicin was effective at lower concentrations when LT was added to the cell cultures. LT (0.1 µg/ml) alone was ineffective for killing the tumor cells. Further, Doxorubicin (below 50 µg/ml) alone was ineffective for killing the tumor cells. When such concentrations of LT and Doxorubicin were combined, however, no viable cells could be detected in the cultures after incubation.

Example 3: Effects of LT and Radiation Therapy in Vivo

A. Radioprotection in Normal Mice

Normal 8 week old BALB/c mice (purchased from Harlan Sprague Dawley) were treated with intraperitoneal injections of LT (10 µg/0.5ml/mouse) at −2 Days and −1 Day prior to radiation on Day 0. Radiation was conducted using $^{137}Cs$ gamma-ray whole body radiation. Groups of mice were radiated with varying doses of radiation ranging from 500 cGy to 800 cGy. Control mice were similarly treated except that 0.5 ml sterile PBS was injected instead of LT.

Figure 5:
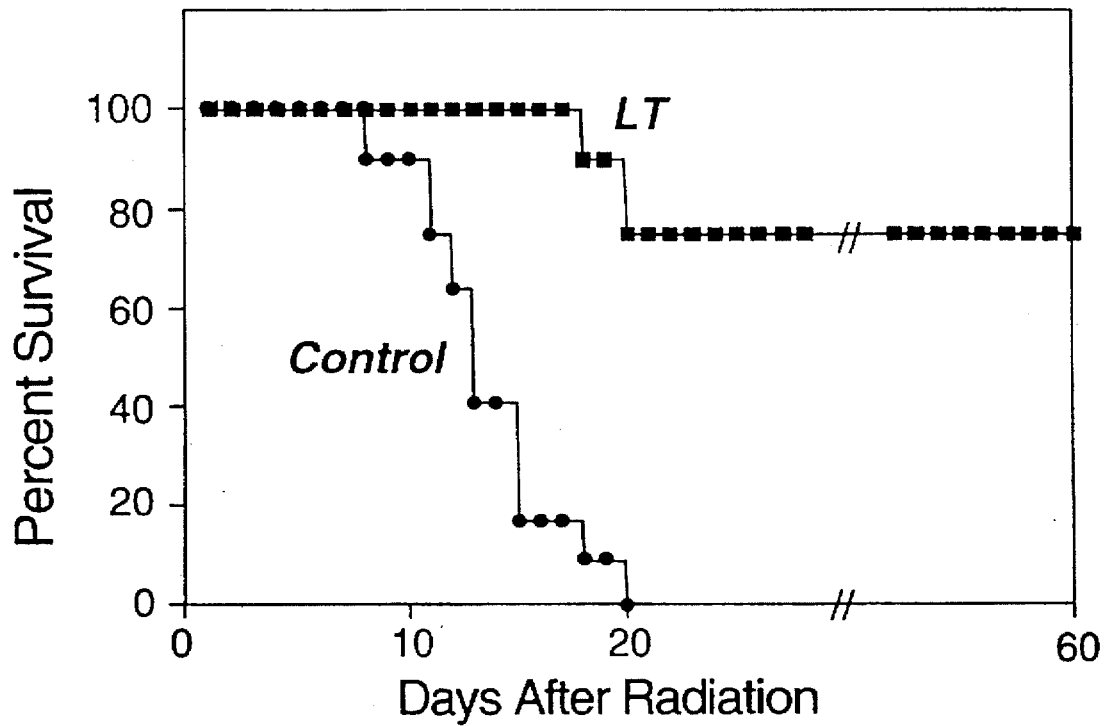
FIG. 5 is a graph showing the effect of LT (10 µg/0.5 ml administered on −2 Days and −1 Day prior to radiation on Day 0) on survival of radiated (750 cGy) normal BALB/c mice.

FIG. 5 shows that at 750 cGy, 80% of the mice receiving LT treatment survived up to 60 days post radiation. 100% of the control animals were dead on Day 20. (FIG. 5). Similar results were observed for nude mice, C57BL/6, and C3H/HeJ mice (radiated with lethal doses of radiation), thus indicating that the radioprotective effect of LT was not strain specific. (data not shown).

Figure 6:
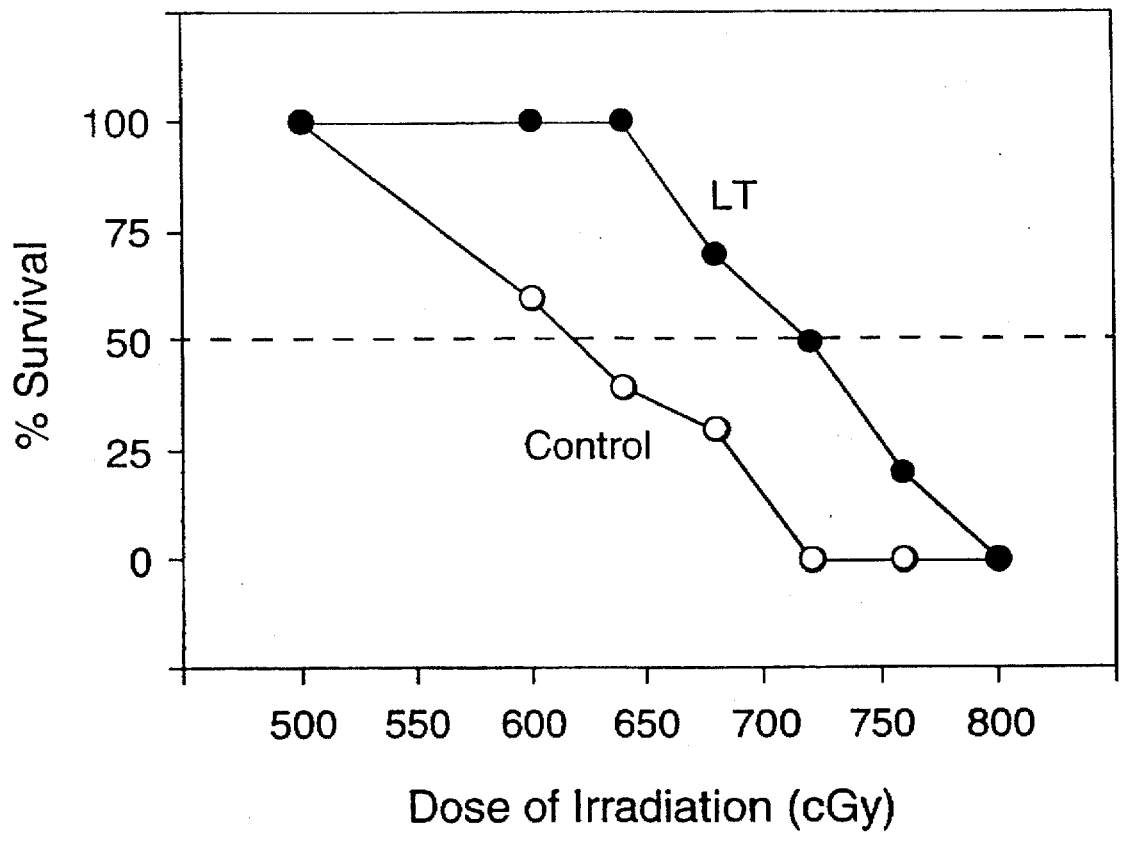
FIG. 6 is a graph showing the effect of LT on survival of normal BALB/c mice radiated with varying doses of $^{137}$Cs gamma-ray whole body radiation.

FIG. 6 is a graph showing the effects of the LT and varying doses of radiation at Day 30 post radiation. The LT treated animals tolerated an approximately 20% increase in radiation dose at the LD50 level. (FIG. 6).

B. Radioprotection in Tumor Bearing Mice

The radioprotective effects of LT were also examined in tumor bearing BALB/c mice. BALB/c mice (purchased from Harlan Sprague Dawley) were injected subcutaneously with murine Meth-A fibrosarcoma cells ($2\times10^5$ cells/mouse) [obtained from Lloyd Old, Memorial Sloan-Kettering Cancer Center, New York, N.Y.; see also, Carswell et al., Proc. Natl. Acad. Sci., 72:3666–3670 (1970)]. The tumors were then allowed to grow for 10 days. Either LT (10 µg/0.5 ml/mouse) or TNF (10 µg/0.5 ml/mouse) was then injected intraperitoneally in the tumor bearing mice at −2 Days and −1 Day prior to radiation on Day 0. The mice were radiated on Day 0 using 750 cGy $^{137}Cs$ gamma-ray whole body radiation. Survival was then observed up to 40 days post radiation.

Figure 7:
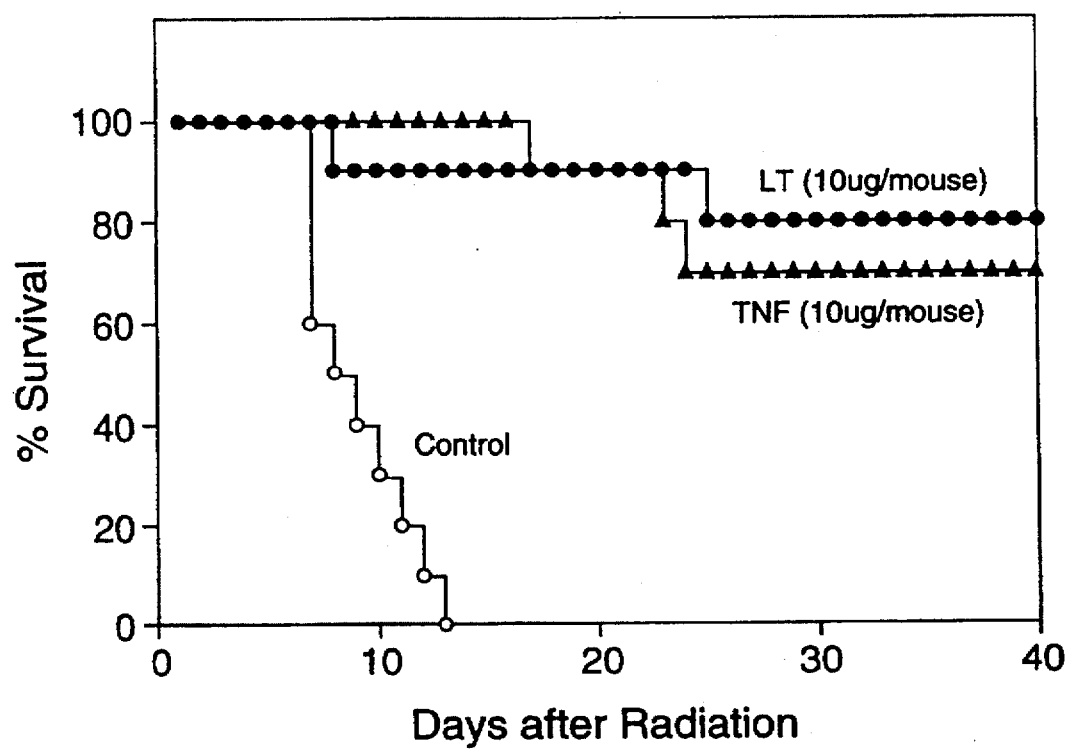
FIG. 7 is a graph showing the effects of LT and TNF on survival of radiated (750 cGy) tumor bearing BALE/c mice.

At Day 12 after radiation treatment, 9/10 (90%) of mice pretreated with LT survived whereas all the control tumor bearing mice (10/10) were dead. (See FIG. 7). At Day 40, 8/10 mice pretreated with LT were alive and free of tumor cells whereas 7/10 TNF-pretreated mice survived (one mouse having detectable tumor).

Figure 8:
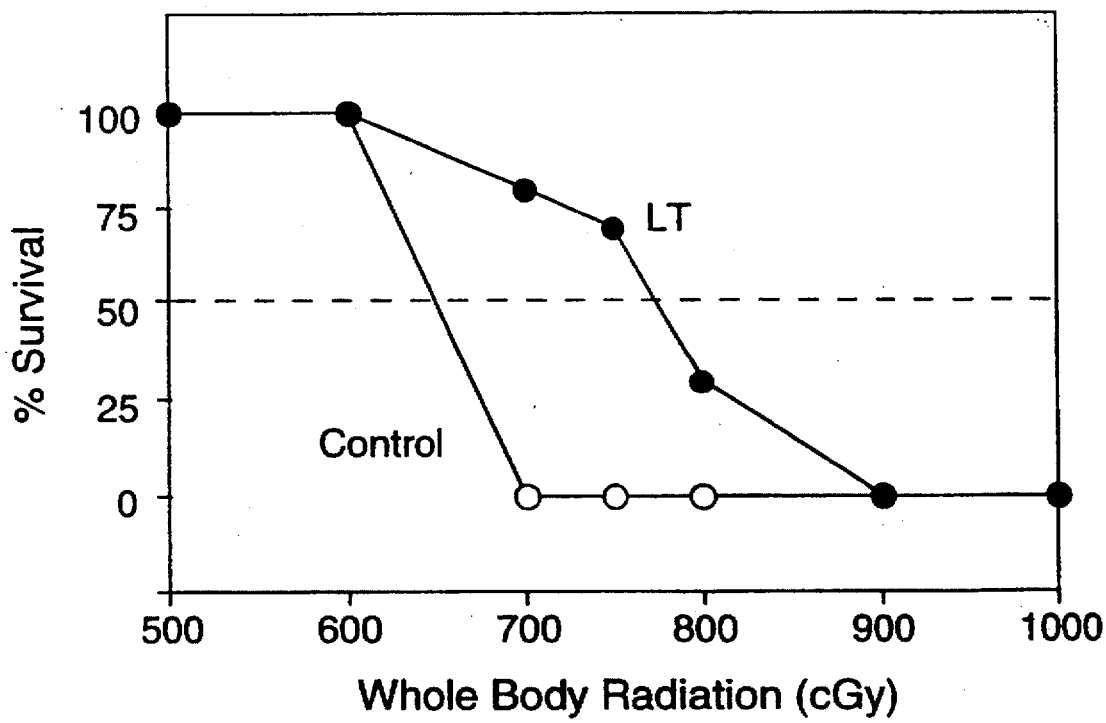
FIG. 8 is a graph showing the effect of LT on survival of tumor bearing BALB/c mice radiated with varying doses of $^{137}$Cs gamma-ray whole body radiation.

A group of the LT treated mice were also radiated with varying doses of radiation. On Day 30 post radiation, it was observed that LT treatment allowed approximately 20% increase in radiation dose to be tolerated at the LD50 level. (FIG. 8).

Figure 9:
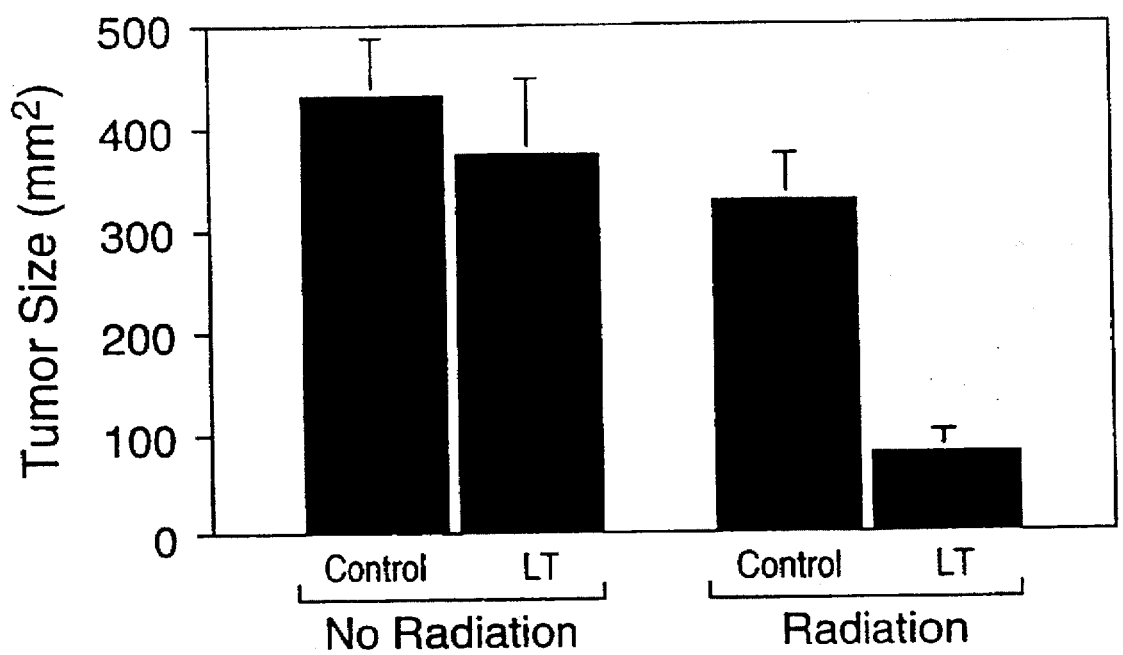
FIG. 9 is a bar diagram showing the effect of LT treatment (prior to radiation) in reducing tumor size in radiated (750 cGy) tumor bearing BALB/c mice.

Pretreatment with LT also enhanced sensitivity of the tumor cells to the radiation treatment. Those mice receiving LT prior to radiation (750 cGy) showed significant reduction in tumor size at Day 7. (See FIG. 9).

C. Effect in Radiated Tumor Bearing Nude Mice

The effects of LT and radiation therapy were examined in tumor bearing nude mice (purchased from Harlan Sprague Dawley) using the protocol described in Example 3, Section B above except that HT 1080 human fibrosarcoma cells (obtained from ATCC, No. CCL 121) were injected subcutaneously into the mice.

The LT treated nude mice had 100% survival (10/10 mice) out to 25 days post radiation treatment. In contrast, 50% of the control mice were dead on Day 15 post radiation, and 100% of the control mice were dead on Day 19 post radiation. (data not shown)

Pretreatment with LT also resulted in enhanced degree of necrosis of the tumors on Day 12, as shown in Table 2 below.

TABLE 2

| LT PRETREATMENT | RADIATION | DEGREE OF NECROSIS | | | |
|---|---|---|---|---|---|
| | | 0 | 1+ | 2+ | 3+ |
| Control | − | 6 | 4 | | |
| LT | − | 5 | 3 | 2 | |
| Control | + | 5 | 5 | | |
| LT | + | | 3 | 2 | 5 |

D. Radiosensitization in Nude Mice Bearing Breast Adenocarcinoma Tumor

The effects of LT and radiation therapy in tumor bearing nude mice were examined by treating mice with LT and radiation therapy and then assaying tumor cells in vitro in a clonogenic assay.

Nude mice (obtained from Harlan Sprague Dawley) were injected subcutaneously with MDA231 human breast adenocarcinoma cells (obtained from ATCC, No. HTB 26) ($10^6$ cells/0.1 ml/mouse) and the tumor cells were allowed to grow for 10 days. LT was injected intraperitoneally (10 µg/0.5 ml/mouse) at −2 Days and −1 Day prior to radiation on Day 0. Control animals were similarly treated except that 0.5 ml sterile PBS was injected instead of LT. The mice were radiated using 1500 cGy $^{137}Cs$ gamma-ray whole body radiation to mimic local radiation dose in humans. One day after radiation treatment, the mice were sacrificed. The tumors were then isolated and aseptically removed from the subcutaneous site.

Each tumor was placed in a sterile petri dish and 1–2 ml Hank's Balanced Salt Solution ("HBSS") containing antibiotic was added to each dish. The tumors were then chopped into small fragments. The contents of the petri dishes were transferred to 125 ml flasks. Approximately 7–8 ml of HBSS was used to rinse the petri dishes and was then added to the 125 ml flasks containing the tumor fragments.

Single cell suspensions of each tumor were prepared by adding 1 ml enzyme digestion solution to each 125 ml flask.

The enzyme digestion solution included HBSS and 6 mg/ml Pronase (purchased from Cal-Biochem), 2 mg/ml DNAse (purchased from Sigma), and 2 mg/ml Collagenase (purchased from Sigma). The enzyme digestion solution and tumor fragments were next incubated for 20 minutes in a warm room on a shaker apparatus. To stop the enzymatic reaction, 7 ml fetal bovine serum was added to each flask. The contents of the flasks were then filtered through sterile gauze to separate out undigested tumor fragments. The filtered cell suspensions were rinsed with cold PBS containing antibiotic and placed in 50 ml conical tubes.

Figure 10:
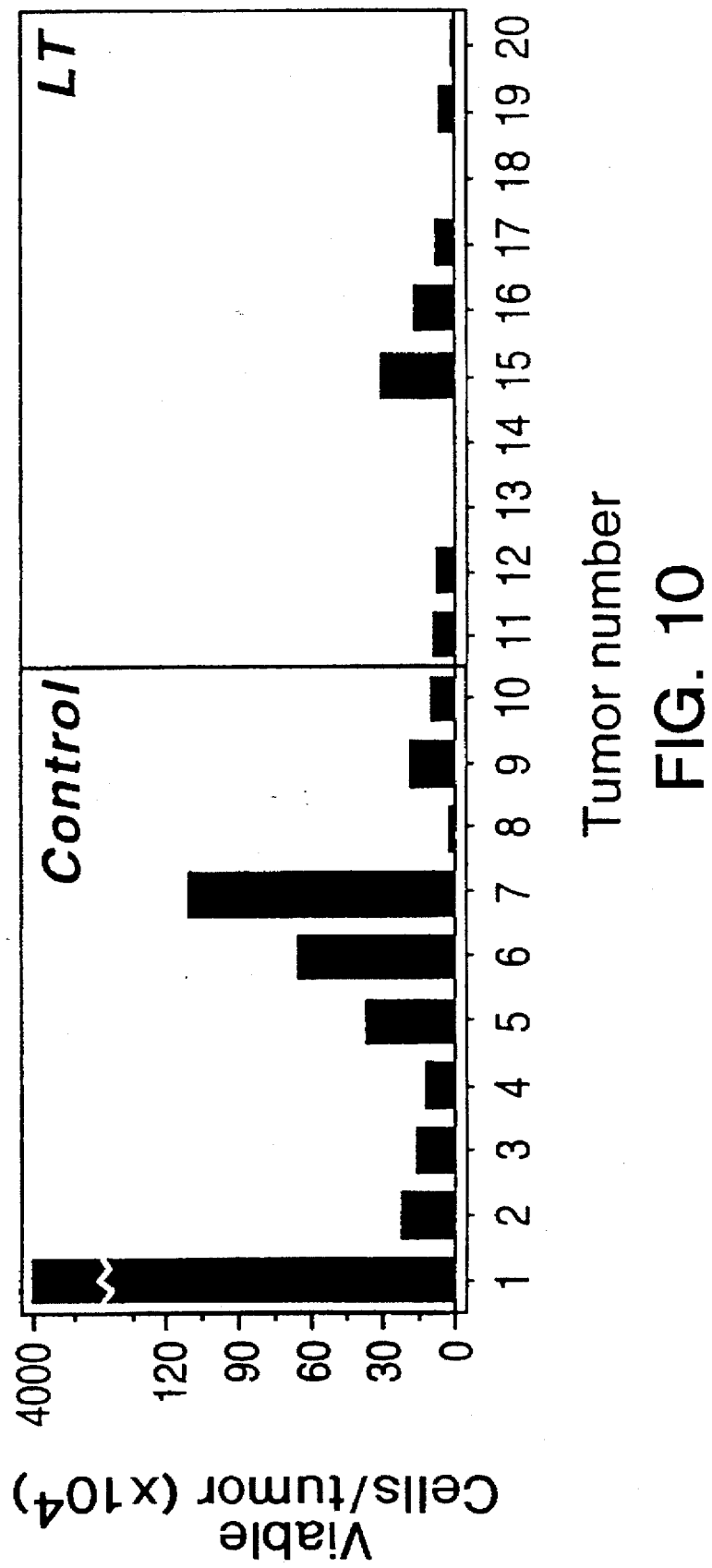
FIG. 10 is a bar diagram showing the effect of LT on tumor cell viability in radiated (1500 cGy) tumor bearing nude mice.

The tumor cells were then tested for cell viability using trypan blue dye exclusion. The LT treated mice showed fewer viable tumor cells remaining after radiation treatment as compared to control animals. (See FIG. 10). Three of ten mice (identified as tumor nos. 13, 14, and 18 on FIG. 10) receiving LT had no detectable viable tumor cells.

Figure 11:
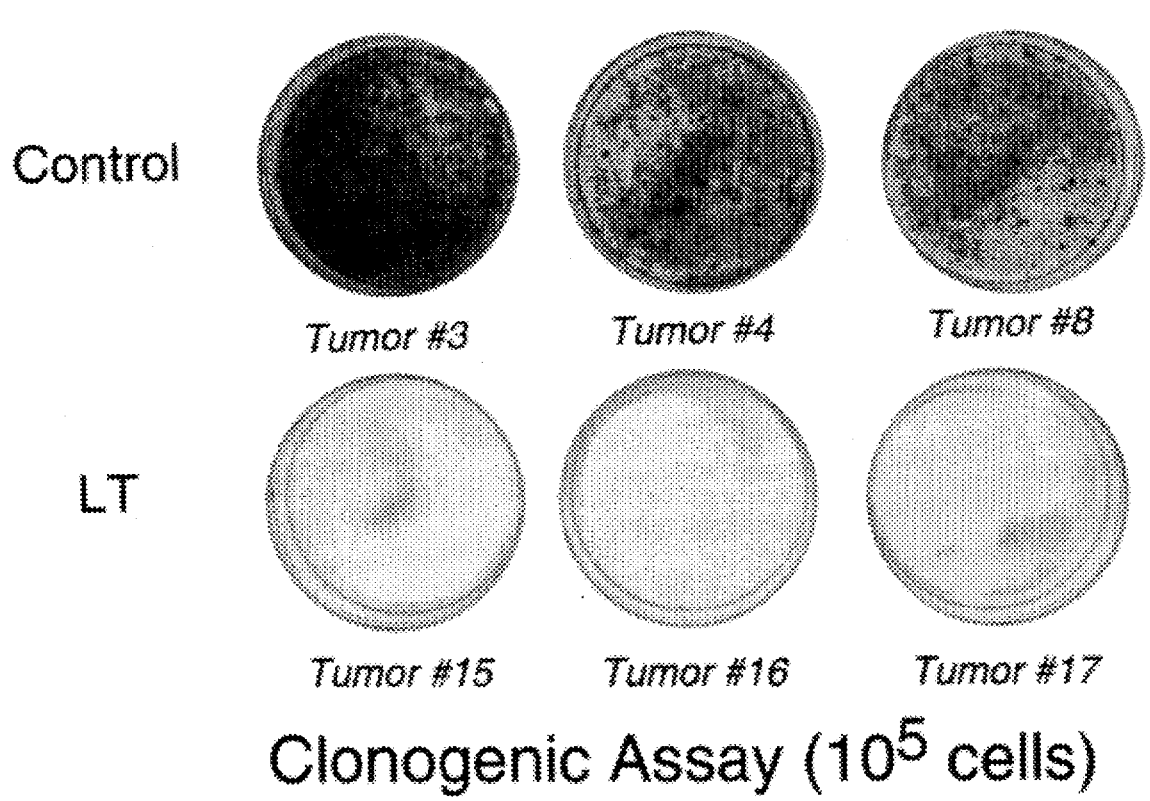
FIG. 11 shows photographs of clonogenic assay culture plates containing either control or LT treated MDA 231 breast adenocarcinoma tumor cells stained with crystal violet.

A portion of each single viable cell suspension was also tested in a clonogenic assay. Viable tumor cells from LT treated tumor nos. 15, 16, and 17 (identified in FIG. 10) and control tumor nos. 3, 4, and 8 (identified in FIG. 10) were plated in high glucose DMEM at a concentration of $10^5$ cells/petri dish and incubated at 37° C. After 2 weeks, cell cultures were stained with 0.5% crystal violet in 20% methanol. As shown in FIG. 11, cells from all three control animals continued to grow. In contrast, none of the LT treated tumor cells grew.

E. Radiosensitization in Nude Mice Bearing Human Primary Tumor

Nude mice were treated essentially as described in Example 3, Section D above, except that the mice were injected with colon cancer cells isolated from a primary tumor in a human patient (designated patient No. 180). The tumor cells were allowed to grow in the nude mice for 14 days. Tumors grew in 12/20 mice injected with the human primary tumor cells.

Figure 12A:
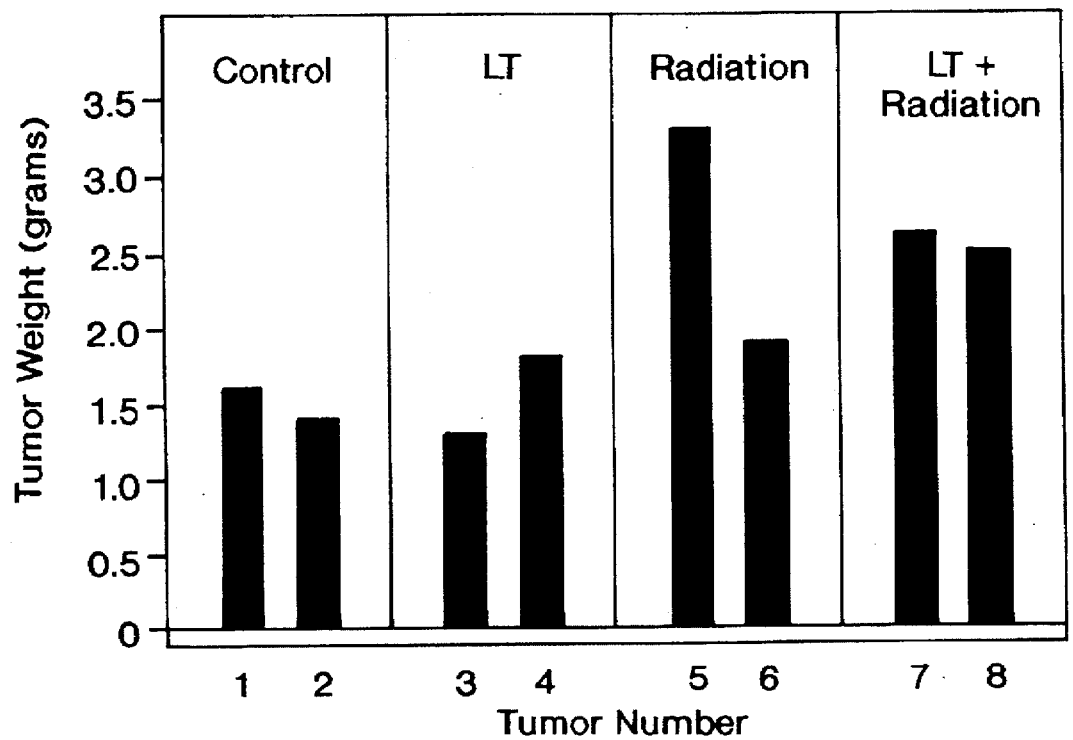
FIG. 12A is a bar diagram showing the effect of LT, radiation, and LT and radiation on tumor weight (grams) of primary human colon tumors in radiated (1500 cGy) tumor bearing nude mice.
Figure 12B:
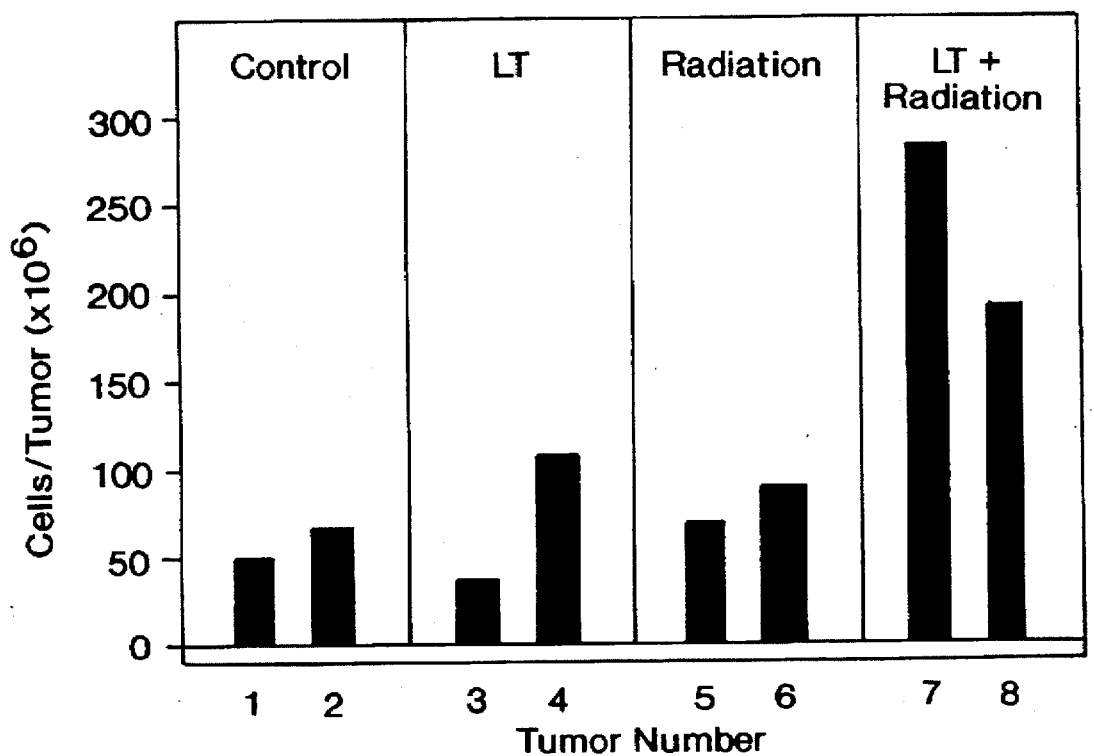
FIG. 12B is a bar diagram showing the effects on total cell yield.
Figure 12C:
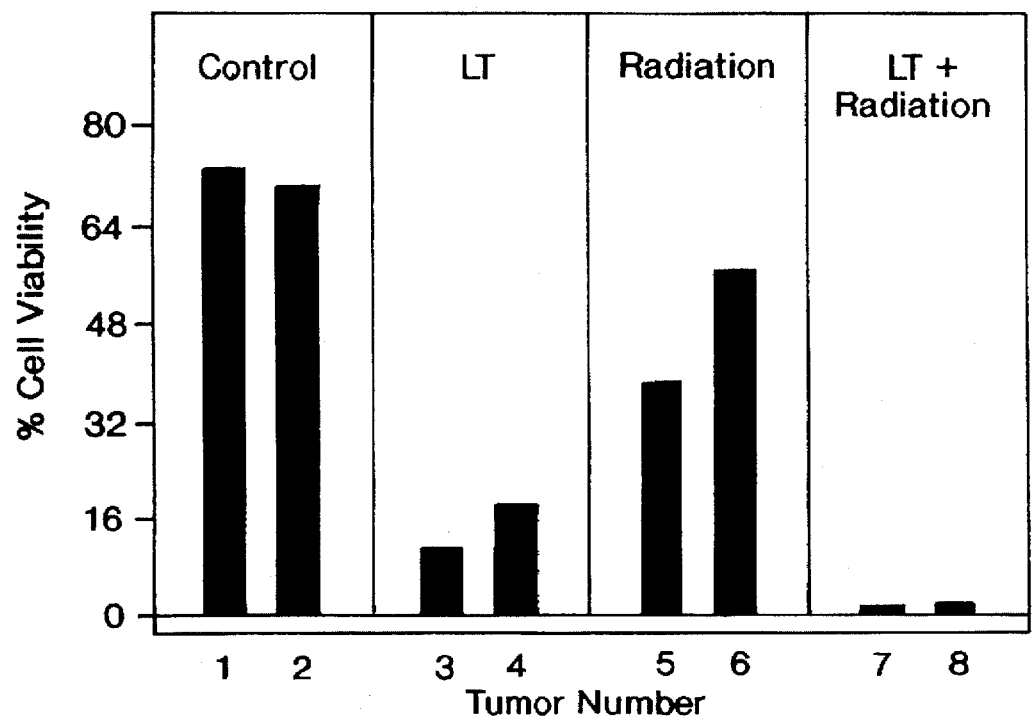
FIG. 12C is a bar diagram showing the effects on cell viability.

One day after irradiation (1500 cGy) treatment, the tumor bearing mice were sacrificed. The tumors were then isolated and aseptically removed from the subcutaneous site. The tumors were first weighed and it was observed that LT treatment did not affect the size (weight) of the intact tumors (FIG. 12A). Each tumor was then chopped into fragments and single cell suspensions were prepared as described in Example 3, Section D above. The single cell suspensions were then counted. As shown in FIG. 12B, LT and radiation treatment did not result in a decrease in the total cell yield from the tumor. However, when the tumor cell suspensions were tested for cell viability using trypan blue dye exclusion, it was found that the LT-radiation treated mice had tumors with significantly lower cell viability as compared to the control mice. (See FIG. 12C).

A portion of each single cell suspension was also tested in a clonogenic assay. Viable tumor cells from the mice were adjusted to a concentration of $10^6$ cells/ml in high glucose DMEM media. Soft agar cultures were prepared by autoclaving a 1% DIFCO Bacto-Agar solution and then incubating the solution at 52° C. The 1% Bacto-Agar solution was mixed with an equal volume of 2× high glucose DMEM media, and 4 ml of the mixture was added to 60 mm petri plates. The agar mixture in the plates was then allowed to solidify. The tumor cells were then plated by adding 100 μl of the cell suspensions (10cells/ml) to the agar-coated plates. Next, a top layer of agar was added to the petri plates. The top layer of agar was prepared by autoclaving a 0.5% DIFCO Bacto-Agar solution and incubating the solution at 52° C. The 0.5% Bacto-Agar solution was mixed with an equal volume of 2× high glucose DMEM media, and 3 ml of the agar mixture was added to each petri plate. The top layer of agar was then allowed to solidify.

Figure 12D:
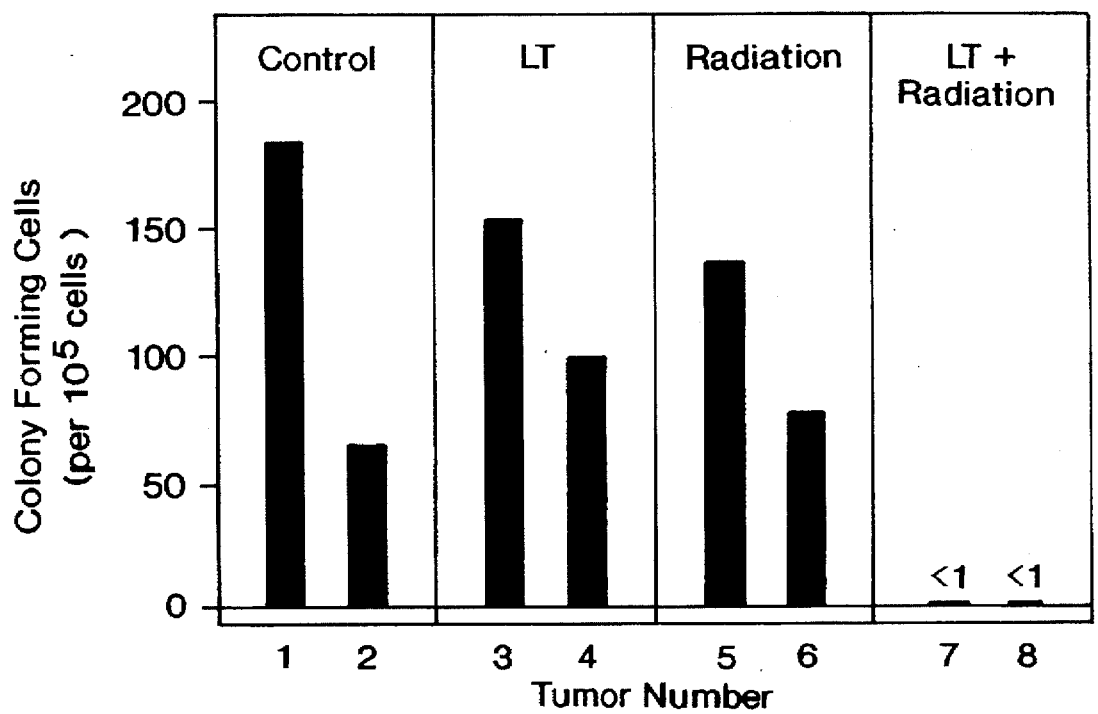
FIG. 12D is a bar diagram showing the effects on numbers of colony forming cells.

The cultures were incubated at 37° C. for two weeks. Next, the tumor cell cultures were stained with 10 mg/ml MTT (3-[4,5 dimethylthiazol-2-yl]-2,5-diphenyltetrazolium bromide) in EtOH. Specifically, 230 μl of the MTT solution was added to 10 ml high glucose DMEM to form a mixture, and 1 ml of the mixture was added to each petri plate. The petri plates were incubated 12–24 hours at room temperature and the number of colonies in each plate was then counted. As shown in FIG. 12D, the tumors from the mice treated with LT and radiation had less than one colony forming cell per $10^5$ cultured tumor cells.

Similar results were obtained in identical experiments testing primary colon tumor cells obtained from another human patient (designated patient No. 179). (data not shown).

F. Effect on Bone Marrow

Nude mice were treated essentially as described in Example 3, Section A above. Eleven days after radiation on Day 0, the mice were sacrificed. Bone marrow cells were collected by dissecting femur bones and flushing the femoral shafts with sterile PBS. The cells were then washed and resuspended in DMEM medium. Bone marrow cellularity was determined by scoring nucleated cells on a hemocytometer after staining with trypan blue.

For the identification of multipotent hematopoietic progenitor cells, $5 \times 10^3$ bone marrow cells from LT treated mice and control mice were cultured in 1% methylcellulose (4,000 mP, Fluka, A. G., Bachs, Switzerland) in DMEM medium supplemented with 15% fetal bovine serum, 0.45 mM monothioglycerol, 2 mM L-glutamine, 15 mg/ml insulin, 200 mg/ml transferrin, 1,000 U IL-1beta, 50 U IL-3 (purchased from Genzyme, Cambridge, Mass.) and either 1 U of GM-CSF or 2.4 U of EPO (IL-1beta, GM-CSF and EPO were purchased from R & D Systems, Minneapolis, Minn.). Cells were cultured in a final volume of 1.5 ml in 35 mm petri plates for 10 days, after which time colony formation was determined using a dissecting microscope.

Figure 13:
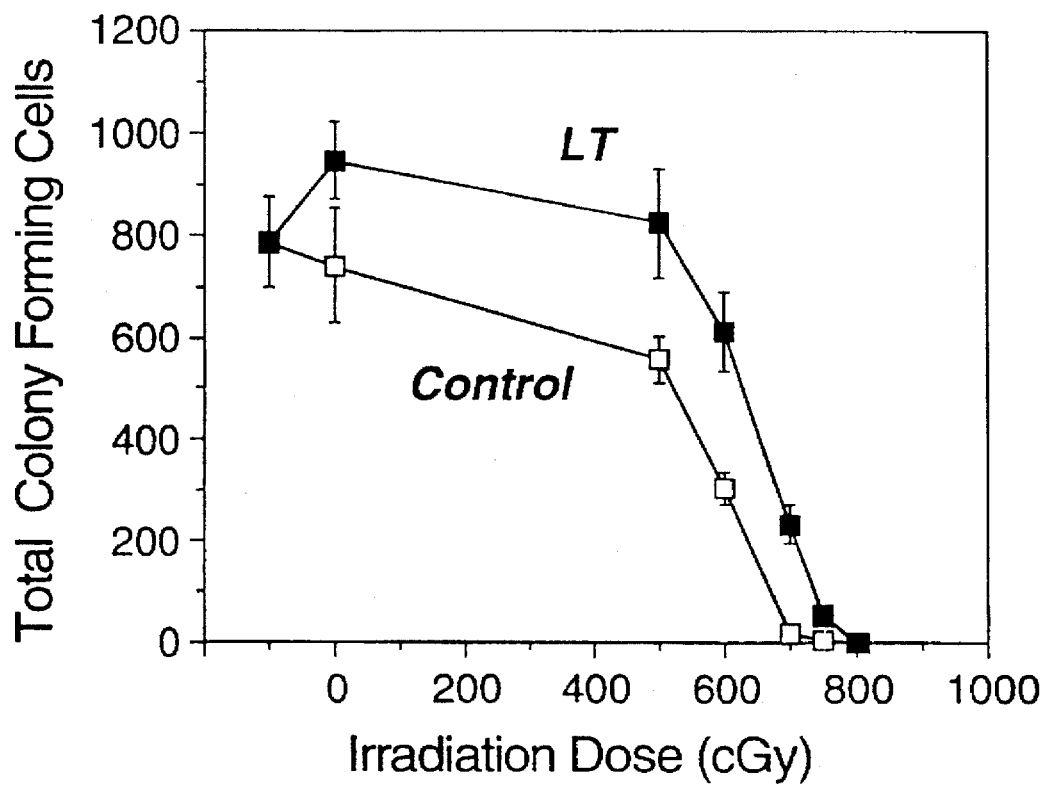
FIG. 13 is a graph showing the effect of LT on numbers of colony forming cells in bone marrow of tumor bearing nude mice radiated with varying doses of $^{137}$Cs gamma-ray whole body radiation.

The results are shown in FIG. 13. Bone marrow from LT-radiation treated mice gave rise to higher numbers of colony forming cells than the control group, indicating LT may protect progenitor, stem cells or/and bone marrow stromal cells against radiation induced damage.

G. Effect on Circulating Platelet Levels

C57BL/6 mice (obtained from Harlan Sprague Dawley) were injected intraperitoneally with 10 μg/0.5 ml/mouse LT at −2 Days and −1 Day prior to radiation at Day 0. Control mice were similarly treated except that sterile PBS was injected instead of LT. The mice were then radiated using 750 cGy $^{137}$Cs gamma-ray whole body radiation.

Blood samples from a randomized number of mice (10) were obtained prior to injecting LT or PBS on −2 Days. These blood samples (40 μl/mouse) were obtained from the orbital sinus of each mouse using micropipettes (Serono Diagnostics, Inc., Allentown, Pa.) and were immediately diluted in 10 ml of diluent (Haema-Line DIFF Silos, Serono-Baker Diagnostics, Inc., Allentown, Pa.). The samples were rocked gently to prevent sedimentation of the cells. Within 1 hour of collection, blood samples were analyzed using a Serono Baker System 9000 hematology analyzer. Blood samples were similarly obtained and analyzed on Day 0 (before radiation) and Days 3, 10, 12, 14, 17, 20, 24, and 28 after radiation. Five animals in each group were bled on alternate time points, with the exception of Day 10, on which all the animals were bled. Animals were not bled more than a total of 5 times throughout the study.

Figure 14:
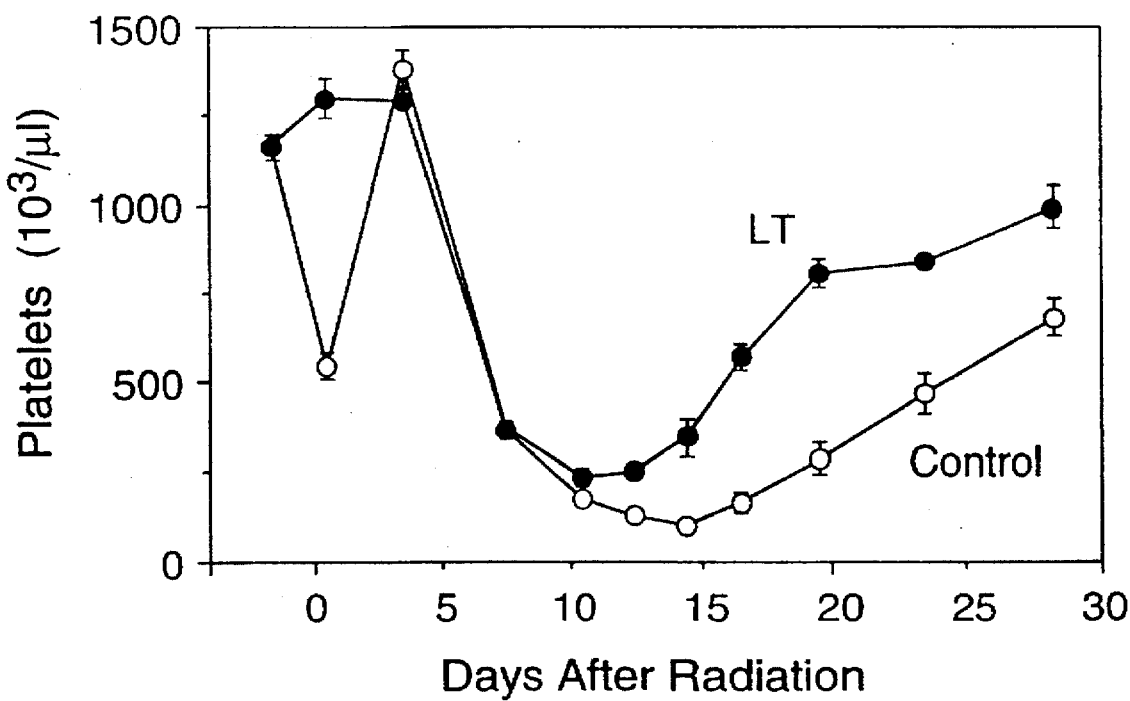
FIG. 14 is a graph showing the effect of LT on circulating platelet levels in radiated (750 cGy) normal C57BL/6 mice.

As shown in FIG. 14, the platelet counts from LT treated mice were significantly higher than the control mice on Days 14, 17, 20, 24 and 28 after radiation. Increased platelet counts were also observed in other strains of mice, such as BALB/c and nude mice, treated with LT prior to lethal radiation. (data not shown).

Example 4: Effects of LT and Radiation Therapy in Vitro

Bone marrow cells from normal BALB/c mice (mice obtained from Harlan Sprague Dawley) and cell lines HL-60 (human promyelocytic leukemia cells obtained from ATCC, No. CCL 240), K-562 (human chronic myelogenous leukemia cells, ATCC No. CCL 243), ME-180 (human epidermoid carcinoma cells, ATCC No. HTB 33), and T-24 (human transitional-cell carcinoma cells, ATCC No. HTB 4) were cultured in RPMI-1640 medium supplemented with 5% fetal calf serum. Test cultures were treated with 1 µg/ml LT. No LT was added to the control cultures. Twelve hours after adding the LT to the test cultures, both test cultures and control cultures were radiated using 1000 cGy $^{137}$Cs gamma-ray radiation. After 72 hours, the cells were tested for viability by trypan blue dye exclusion. The results of the viability testing are shown in Table 3 below.

TABLE 3

| CELLS | % VIABILITY | |
|---|---|---|
|  | CONTROL | LT TREATMENT |
| Normal BALB/c Bone Marrow | 28 +/− 7 | 65 +/− 6 |
| HL-60 | 25 +/− 3 | <1 |
| K-562 | 31 +/− 5 | <1 |
| ME-180 | 22 +/− 2 | <1 |
| T-24 | 47 +/− 11 | <1 |

The cancer cell lines treated with LT prior to radiation had <1% viability 72 hours after radiation treatment. The normal BALB/c bone marrow cells treated with LT prior to radiation, in contrast, showed enhanced viability after radiation.

What is claimed is:

1. A method of treating a mammal having cancer, comprising administering to a mammal diagnosed as having cancer chemotherapy and an effective amount of lymphotoxin which sensitizes the mammal's cancerous cells to the chemotherapy and protects the mammal's non-cancerous cells.

2. The method of claim 1 wherein the lymphotoxin is administered to the mammal concurrently with the chemotherapy.

3. The method of claim 1 wherein the lymphotoxin is administered to the mammal prior to administration of the chemotherapy.

4. The method of claim 1 wherein the lymphotoxin is histidyl amino-terminal lymphotoxin comprising amino acids 24–171 of human lymphotoxin.

5. The method of claim 1 wherein the lymphotoxin is leucyl amino-terminal lymphotoxin comprising amino acids 1–171 of human lymphotoxin.

6. The method of claim 1 wherein the chemotherapy comprises Doxorubicin.

7. The method of claim 1 wherein the cancer is lymphoma.

8. The method of claim 1 wherein the cancer is carcinoma.

9. The method of claim 1 wherein the cancer is colon cancer.

10. The method of claim 1 wherein the cancer is pancreatic cancer.

11. The method of claim 10 wherein the chemotherapy is 5-fluorouracil.

12. The method of claim 1 wherein the cancer is lung cancer.

13. The method of claim 1 wherein the cancer is breast cancer.

14. The method of claim 1 wherein the chemotherapy is 5-fluorouracil.

15. A method of treating a mammal having cancer, comprising administering to a mammal diagnosed as having cancer radiation therapy and an effective amount of lymphotoxin which sensitizes the mammal's cancerous cells to the radiation therapy and protects the mammal's non-cancerous cells.

16. The method of claim 15, wherein the lymphotoxin is administered to the mammal prior to administration of the radiation therapy.

17. The method of claim 15 wherein the lymphotoxin is histidyl amino-terminal lymphotoxin comprising amino acids 24–171 of human lymphotoxin.

18. The method of claim 15 wherein the lymphotoxin is leucyl amino-terminal lymphotoxin comprising amino acids 1–171 of human lymphotoxin.

19. The method of claim 15 wherein the cancer is sarcoma.

20. The method of claim 15 wherein the cancer is carcinoma.

21. The method of claim 15 wherein the cancer is colon cancer.

22. The method of claim 15 wherein the cancer is leukemia.

23. An article of manufacture, comprising:

a container;

a label on said container; and a composition contained within said container; wherein the composition includes an active agent for treating cancer in a mammal, the label on said container indicates that the composition is for use with chemotherapy or radiation therapy to treat the cancer, and the active agent in said composition comprises an effective amount of lymphotoxin which sensitizes the mammal's cancerous cells to the chemotherapy or radiation therapy and protects the mammal's non-cancerous cells.

24. The article of manufacture of claim 23 further comprising instructions for administering the lymphotoxin and chemotherapy or radiation therapy to a mammal.

* * * * *